US012286397B1

(12) United States Patent
Malaibari et al.

(10) Patent No.: US 12,286,397 B1
(45) Date of Patent: Apr. 29, 2025

(54) METHOD OF CRACKING A HYDROCARBON

(71) Applicant: KING FAHD UNIVERSITY OF PETROLEUM AND MINERALS, Dhahran (SA)

(72) Inventors: Zuhair Omar Malaibari, Dhahran (SA); Ijaz Hussain, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 18/777,864

(22) Filed: Jul. 19, 2024

(51) Int. Cl.
*C07C 4/06* (2006.01)
*B01J 29/70* (2006.01)
*B01J 35/50* (2024.01)
*B01J 35/61* (2024.01)
*B01J 35/63* (2024.01)
*B01J 35/64* (2024.01)
(Continued)

(52) U.S. Cl.
CPC ............ *C07C 4/06* (2013.01); *B01J 29/7038* (2013.01); *B01J 35/50* (2024.01); *B01J 35/615* (2024.01); *B01J 35/633* (2024.01); *B01J 35/647* (2024.01); *B01J 35/77* (2024.01); *B01J 37/0018* (2013.01); *B01J 37/033* (2013.01); *B01J 37/10* (2013.01); *C01B 39/48* (2013.01); *C01P 2002/60* (2013.01); *C01P 2002/72* (2013.01); *C01P 2002/86* (2013.01); *C01P 2004/03* (2013.01); *C01P 2004/24* (2013.01); *C01P 2006/12* (2013.01); *C01P 2006/14* (2013.01); *C01P 2006/16* (2013.01); *C07C 2529/70* (2013.01)

(58) Field of Classification Search
None
See application file for complete search history.

(56) References Cited

U.S. PATENT DOCUMENTS

| 6,843,977 B2 | 1/2005 | Pinnavaia et al. |
| 11,180,704 B2 | 11/2021 | Van Iersel et al. |
| 2012/0027673 A1* | 2/2012 | Larsen .................. C01B 39/48 423/702 |

FOREIGN PATENT DOCUMENTS

| CN | 102039157 B | 7/2012 |
| TW | I359696 B | 3/2012 |

OTHER PUBLICATIONS

Cao et al. "'Desert Rose' MCM-22 microsphere: Synthesis, formation mechanism and alkylation performance" and Supplemental Information Microporous and Mesoporous Materials, vol. 315, 2021. (Year: 2021).*

(Continued)

*Primary Examiner* — In Suk C Bullock
*Assistant Examiner* — Alyssa L Cepluch
(74) *Attorney, Agent, or Firm* — Oblon, McClelland, Maier & Neustadt, L.L.P.

(57) ABSTRACT

A method of cracking a hydrocarbon including contacting the hydrocarbon with a catalyst; where on the contacting, the hydrocarbon is cracked into a plurality of compounds, each having a smaller number of carbon atoms than the hydrocarbon. The catalyst includes an aluminosilicate zeolite, the aluminosilicate zeolite includes a weight ratio of $SiO_2$ to $Al_2O_3$ of 10-200:1. Particles of the aluminosilicate zeolite have a flake shape with an average longest dimension of 10 nanometers (nm) to 50 nm and the flakes are stacked on top of one another.

19 Claims, 15 Drawing Sheets

(51) Int. Cl.
*B01J 35/77* (2024.01)
*B01J 37/00* (2006.01)
*B01J 37/03* (2006.01)
*B01J 37/10* (2006.01)
*C01B 39/48* (2006.01)

(56) References Cited

OTHER PUBLICATIONS

Hao et al. "Synthesis of ITQ-2 Zeolites and Catalytic Performance in n-Dodecane Cracking" Chinese Journal of Chemical Engineering, vol. 22, Issue 8, 2014 pp. 869-874 (Year: 2014).*

Mastropietro et al. "Low temperature synthesis of nanosized NaY zeolite crystals from organic-free gel by using supported seeds" RSC Adv. 2014, 4, 21951-21957 (Year: 2014).*

Wang et al., "Catalytic cracking of n-hexane for producing propylene on MCM-22 zeolites", Applied Catalysis A: General, vol. 504, Sep. 5, 2015, pp. 192-202.

Kolfar et al., "Micro/mesoporous aluminosilicate composites from zeolite MCM-22 precursor," Microporous and Mesoporous Materials, vol. 99, Issues 1-2, Feb. 1, 2007, pp. 37-46.

Chu et al., "Nestlike Hollow Hierarchical MCM-22 Microspheres: Synthesis and Exceptional Catalytic Properties", Chemistry of Materials, vol. 22, Issue 9, Mar. 29, 2010, pp. 2757-2763.

\* cited by examiner

METHOD OF CRACKING A HYDROCARBON

STATEMENT OF PRIOR DISCLOSURE BY INVENTOR

Aspects of the present disclosure are described in M. A. Firdaus, Z. Malaibari, O. Muraza, J. Nasser, A. I. Bakare, I. Hussain, and H. Alasiri "Catalytic conversion of n-Dodecane to lower olefins hydrogen carriers over bran-shaped modified MCM-22 zeolite catalyst: $SiO_2/Al_2O_3$ ratio effects"; International Journal of Hydrogen Energy; 2024; 52; 635-648, incorporated herein by reference in its entirety.

STATEMENT OF ACKNOWLEDGEMENT

Support provided by the Center for Refining and Advanced Chemicals, Research Institute at King Fahd University of Petroleum and Minerals (KFUPM) is gratefully acknowledged.

BACKGROUND

Technical Field

The present disclosure is directed to cracking hydrocarbons, and more particularly, to a method of cracking hydrocarbons using zeolites.

Description of Related Art

The "background" description provided herein is to present the context of the disclosure generally. Work of the presently named inventors, to the extent it is described in this background section, as well as aspects of the description that may not otherwise qualify as prior art at the time of filing, are neither expressly nor impliedly admitted as prior art against the present invention.

Global population growth and improved living standards have led to an increased demand for chemicals, particularly light olefins. These compounds are used in the production of various products such as polyethylene, ethylbenzene, polypropylene, plastics, textiles, and fine chemicals. Additionally, there is an increasing need for oil feedstocks and petrochemicals, resulting in a surge in the conversion of heavy oil into lighter hydrocarbons for industrial applications.

Traditionally, crude oil fractions and byproducts of natural gas processing have served as the primary sources for olefin production. Conventional methods employed for light olefin production include steam cracking (SC), fluidized catalytic cracking (FCC) utilizing zeolites, deep catalytic cracking (DCC), and methanol-to-olefins (MTO). Steam cracking, in particular, is the prevailing process employed in olefin manufacturing. However, due to declining petroleum reserves and increased public awareness of petrochemical pollution, greener technologies and alternative sources for olefin production are explored.

Naphtha cracking process has potential to convert naphtha into light olefins by the use of various catalytic materials, most notably zeolites. In general, zeolites are aluminosilicates typically made by mixing silica, alumina, and alkaline elements with an organic structure-directing agent. The source of the entities employed in the creation of manufactured zeolites may affect the physicochemical qualities of the final product, thereby effecting the refining characteristics, including acidity, texture, structure, morphology, and catalytic efficiency. Different aluminum, silicon, and template sources, as well as a wide range of heating regimes, have all been investigated in numerous research studies that focus on improving zeolite properties.

Zeolites are the most effective catalysts for aromatization, cyclization, cracking, and reforming reactions due to their three-dimensional channel structure, including straight and zigzag channels. Recently, catalytic cracking of n-dodecane to subsequent chemicals is done to yield light olefins and aromatics. N-dodecane comes from crude oil and may be derived from lignocellulose-based biomass sources. Generating these long-chain hydrocarbons through plant or vegetable oil may provide an alternative to oil reserves and may be an economical and efficient process. Despite numerous research efforts, the catalytic cracking of n-dodecane using zeolites is a significant challenge in terms of achieving high conversion and selectivity towards light olefins.

Therefore, a need arises to enhance the catalytic properties of zeolites by modifying their physical and chemical characteristics, aiming to improve their efficiency and selectivity in producing light olefins. Hence, one object of the present disclosure is to provide a method for cracking hydrocarbons using modified zeolites that may circumvent the aforementioned drawbacks.

SUMMARY

In an exemplary embodiment, a method of cracking a hydrocarbon is described. The method includes contacting the hydrocarbon with a catalyst; as such, on contacting the hydrocarbon, the hydrocarbon is cracked into a plurality of compounds, each having a smaller number of carbon atoms than the hydrocarbon. The catalyst includes an aluminosilicate zeolite, the aluminosilicate zeolite includes a weight ratio of $SiO_2$ to $Al_2O_3$ of 10:1 to 200:1. Particles of the aluminosilicate zeolite have a flake shape with an average longest dimension of 10 nanometers (nm) to 50 nm, and the flakes are stacked on top of one another.

In some embodiments, the catalyst has an MCM-22 crystal phase.

In some embodiments, the catalyst has a relative crystallinity of 50% to 100%.

In some embodiments, the catalyst has an average crystal size of 10 nm to 30 nm.

In some embodiments, the catalyst has a Brunauer-Emmett-Teller (BET) surface area of 400 $m^2/g$ to 500 $m^2/g$.

In some embodiments, the catalyst has an external surface area of 100 $m^2/g$ to 150 $m^2/g$.

In some embodiments, the catalyst has an average pore size of 2 nm to 5 nm.

In some embodiments, the catalyst has a mesopore volume of 0.1 $cm^3/g$ to 0.3 $cm^3/g$ and a micropore volume of 0.01 $cm^3/g$ to 0.2 $cm^3/g$.

In some embodiments, the catalyst includes 0.1 percent by weight (wt. %) to 5 wt. % Al, 40 wt. % to 50 wt. % Si, and 50 wt. % to 60 wt. % O, based on a total weight of the catalyst.

In another exemplary embodiment, the catalyst has an acid density of 0.2 milli moles per gram (mmol/g) to 0.6 mmol/g.

In some embodiments, the method of contacting the hydrocarbon is at a temperature of 200° C. to 600° C.

In some embodiments, the hydrocarbon has 5 to 20 carbon atoms.

In some embodiments, the hydrocarbon is n-dodecane.

In some embodiments, the catalyst has a conversion rate of at least 90% to the plurality of compounds.

In some embodiments, the plurality of compounds is at least one selected from the group consisting of olefins and paraffins.

In some embodiments, the plurality of compounds includes both olefins and paraffins, and a ratio of paraffins to olefins is 1:1 to 2:1.

In some embodiments, the plurality of compounds includes at least 30% linear paraffins.

In some embodiments, the plurality of compounds includes 1 to 6 carbon atoms.

In some embodiments, the catalyst has a weight ratio of $SiO_2$ to $Al_2O_3$ of 28.8:1; the catalyst has a conversion rate of 99.9% to the plurality of compounds; the hydrocarbon is n-dodecane, the plurality of compounds includes at least 25% of paraffin compounds having 4 carbon atoms, and the plurality of compounds includes at least 15% of olefin compounds having 4 carbon atoms.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
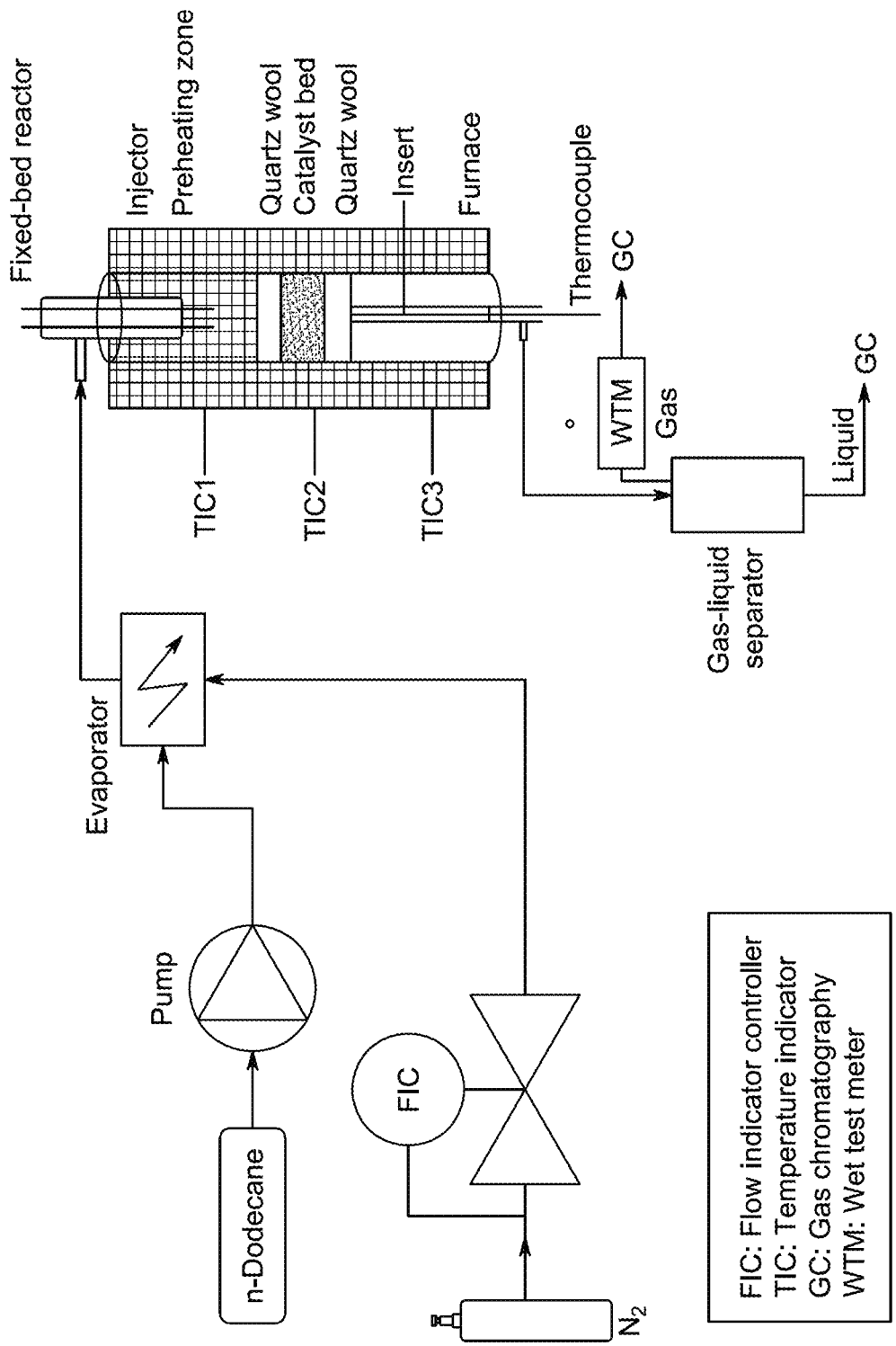
FIG. 1 is a schematic diagram illustrating an experimental setup for the catalytic cracking of n-dodecane to olefins, according to certain embodiments.

In the drawings, reference numerals designate identical or corresponding parts throughout the several views. Further, as used herein, the words "a," "an," and the like generally mean "one or more" unless stated otherwise.

Where a numerical limit or range is stated herein, the endpoints are included. Also, all values and subranges within a numerical limit or range are specifically included as if explicitly written out.

Furthermore, the terms "approximately," "approximate," "about," and similar terms generally refer to ranges that include the identified value within a margin of 20%, 10%, or preferably 5%, and any values therebetween.

As used herein, the term "catalyst" refers to the substance that speeds up a chemical reaction without being consumed in the process or a person or thing that precipitates an event or change. Catalysts may include but are not limited to, homogeneous catalysts, heterogeneous catalysts, enzymes, acid catalysts, base catalysts, photochemical catalysts, electrocatalysts, and biocatalysts.

As used herein, the term 'mesopore', refers to pores having a largest dimension of 2-50 nm.

As used herein, the term 'micropore', refers to pores having a largest dimension up to 2 nm.

As used herein, the term 'olefins', also known as alkenes, are unsaturated hydrocarbons containing at least one carbon-carbon double bond in their molecular structure. The general formula for olefins is $C_nH_{2n}$, where 'n' is the number of carbon atoms. Due to their double bond, olefins can undergo addition reactions, where atoms or groups of atoms are added to the carbon-carbon double bond. Ethylene ($C_2H_4$) and propylene ($C_3H_6$) are common examples of olefins. Olefins are widely used in the production of plastics, detergents, synthetic rubber, and various other industrial chemicals.

As used herein, the term 'paraffins', also known as alkanes, are saturated hydrocarbons consisting of only single bonds between carbon atoms. The general formula for paraffins is $C_nH_{2n+2}$, where 'n' is the number of carbon atoms. Paraffins are characterized by their relatively inert nature, low reactivity, and high stability. They are often found in natural gas and petroleum deposits and are major components of gasoline, diesel fuel, and other petroleum products. Examples of paraffins include methane ($CH_4$), ethane ($C_2H_6$), propane ($C_3H_8$), and butane ($C_4H_{10}$).

As used herein, the term 'linear paraffin,' also known as normal paraffin or n-paraffins, are straight-chain saturated hydrocarbons. These hydrocarbons have a linear arrangement of carbon atoms, meaning that each carbon atom is connected to no more than two other carbon atoms in the chain, with the remaining bonds attached to hydrogen atoms. Examples of linear paraffins include methane ($CH_4$), ethane ($C_2H_6$), propane ($C_3H_8$), butane ($C_4H_{10}$), and so on, with each subsequent member of the series having an additional carbon atom.

Aspects of the present disclosure are directed to a modified MCM-22 catalyst (also referred to as the catalyst) for catalytic conversion of hydrocarbons, particularly n-dodecane, to olefins and paraffins. The catalyst of the present disclosure has a high surface area and a high mesopore volume, leading to a high conversion of n-dodecane.

According to the first aspect of the present disclosure, a zeolitic material catalyst is described. As used herein, the term "zeolitic material" or "zeolitic framework" refers to a material having the crystalline structure or three-dimensional framework of, but not necessarily the elemental composition of, a zeolite. Zeolites are porous silicate or aluminosilicate minerals that occur in nature. Elementary building units of zeolites are $SiO_4$ (and if appropriate, $AlO_4$) tetrahedra. Adjacent tetrahedra are linked at their corners via a common oxygen atom, which results in an inorganic macromolecule with a three-dimensional framework (frequently referred to as the zeolite framework). The three-dimensional framework of a zeolite also includes channels, channel intersections, and/or cages having dimensions in the range of 0.1-10 nanometers (nm), preferably 0.2-5 nm, more preferably 0.2-2 nm. Water molecules may be present inside these channels, channel intersections, and/or cages. Zeolites that are devoid of aluminum may be referred to as "all-silica zeolites" or "aluminum-free zeolites." Some zeolites which are substantially free of, but not devoid of, aluminum is referred to as "high-silica zeolites". Sometimes, the term "zeolite" is used to refer exclusively to aluminosilicate materials, excluding aluminum-free zeolites or all-silica zeolites.

In some embodiments, the zeolitic material has a three-dimensional framework that is at least one zeolite framework selected from the group consisting of a 4-membered ring zeolite framework, a 5-membered ring zeolite framework, a 6-membered ring zeolite framework, a 10-membered ring zeolite framework, and a 12-membered ring zeolite framework. The zeolite may have a natrolite framework (e.g. gonnardite, natrolite, mesolite, paranatrolite, scolecite, and tetranatrolite), edingtonite framework (e.g. edingtonite and kalborsite), thomsonite framework, analcime framework (e.g., analcime, leucite, pollucite, and wairakite), phillipsite framework (e.g., harmotome), gismondine framework (e.g., amicite, gismondine, garronite, and gobbinsite), chabazite framework (e.g., chabazite-series, herschelite, willhendersonite, and SSZ-13), faujasite framework (e.g., faujasite-series, Linde type X, and Linde type Y), mordenite framework (e.g., maricopaite and mordenite), heulandite framework (e.g., clinoptilolite and heulandite-series), stilbite framework (e.g., barrerite, stellerite, and stilbite-series), brewsterite framework, or cowlesite framework.

In some embodiments, the zeolitic material having a zeolite framework is selected from the group consisting of MCM-22, PSH-3, SSZ-25, ERB-1, ITQ-1, ITQ-2, MCM-36, MCM-49, MCM-56, UZM-8, and mixtures of any two or more thereof. In a preferred embodiment, the zeolitic material is MCM-22. Mobil invented MCM-22 zeolite, a type of MWW zeolite with 10-membered ring pore openings and a layered structure with two independent pore channels. One consists of two dimensional sinusoidal 10-membered ring slightly elliptical channels, and the other has a super cylindrical cage of 12-membered ring between layers. The outer surface crystals are formed by half super cages, which are accessible by 10-membered ring channels. MCM-22 includes both $SiO_4$ and $AlO_4$ tetrahedra as building blocks.

In some embodiments, pore channels of the zeolite contain a cationic ion exchange group, for example, ammonium ($NH_4^+$). In some embodiments, the ammonium cationic ion exchange group is transitioned to $H^+$ to form the H form of the zeolite. In a preferred embodiment, the H form is prepared by calcining the zeolite powder at a temperature range of 500-600° C., preferably 550° C., to obtain the H form of the zeolite.

In some embodiments, the weight ratio of $SiO_2$ to $Al_2O_3$ used to make the catalyst is in the range of 10:1 to 200:1, preferably 18:1, 28:1, 56:1, 113:1, or 170:1. MCM-22 itself has a weight ratio of $SiO_2$ to $Al_2O_3$ of 56.6:1, however, the ratio can be modified to adjust the properties of the material. In an embodiment, the weight ratio of $SiO_2$ to $Al_2O_3$ in the catalyst is about 15-20, preferably 16-19, preferably 18.9. In another embodiment, the weight ratio of $SiO_2$ to $Al_2O_3$ in the catalyst is 25-30, preferably 26-29, preferably 28.8. In yet another embodiment, the weight ratio of $SiO_2$ to $Al_2O_3$ in the catalyst is 50-60, preferably 52-58, preferably 54-57, preferably about 56.6. In another embodiment, the weight ratio of $SiO_2$ to $Al_2O_3$ in the catalyst is 110-115, preferably 111-114, preferably about 113.2. In yet another embodiment, the weight ratio of $SiO_2$ to $Al_2O_3$ in the catalyst is 165-175, preferably 167-170, preferably about 169.8. In a most preferred embodiment, the weight ratio of $SiO_2$ to $Al_2O_3$ in the catalyst is 28.8.

In an embodiment, the aluminosilicate zeolite includes a weight ratio of silicon (Si) to aluminum (Al). In an embodiment, the weight ratio of Si to Al in the aluminosilicate zeolite is about 10-15, preferably 11-14, preferably 12-13, preferably 12.18. In another embodiment, the weight ratio of Si to Al in the aluminosilicate zeolite is about 20-25, preferably 21-24, preferably 22-23.5, preferably about 23.11. In yet another embodiment, the weight ratio of Si to Al in the aluminosilicate zeolite is about 65-70, preferably 66-69, preferably about 66.55. In one more embodiment, the weight ratio of Si to Al in the aluminosilicate zeolite is about 120-130, preferably 121-129, preferably 122-128, preferably 123-127, preferably 124-126, preferably about 125.41. In yet another embodiment, the weight ratio of Si to Al in the aluminosilicate zeolite is about 190-195, preferably 191-194, preferably 192-193.5, preferably about 193.13. $SiO_2$ to $Al_2O_3$ In some embodiments, the particles of the zeolite have a morphological shape, such as but not limited to rods, spheres, wires, crystals, rectangles, triangles, pentagons, hexagons, prisms, disks, cubes, ribbons, blocks, beads, toroids, discs, barrels, granules, whiskers, foils, powders, boxes, stars, tetrapods, belts, flowers, etc. and mixtures thereof. In some embodiments, variations in the weight ratio of $SiO_2$ to $Al_2O_3$ result in variations in the morphology. In a preferred embodiment, the particles of the zeolite have a flake shape with an average longest dimension of 10 nanometers (nm) to 100 nm, more preferably 20-90 nm, 30-80 nm, 40-70 nm, or 50-60 nm and a thickness of 1-10 nm, preferably 2-9 nm, 3-8 nm, 4-7 nm, or 5-6 nm. In a preferred embodiment, the zeolite flakes are stacked on top of one another to form larger aggregates having an average size of 0.5-2 μm, preferably 0.75-1.5 μm, or about 1 μm.

In some embodiments, the catalyst includes 0.1 percent by weight (wt. %) to 5 wt. %, more preferably 1.5 wt. % to 2 wt. %, and yet more preferably 1.95 wt. % Al; 40 wt. % to 50 wt. %, more preferably 42 wt. % to 46 wt. %, and yet more preferably 45.02 wt. % Si; and 50 wt. % to 60 wt. %, more preferably 52 wt. % to 55 wt. %, and yet more preferably 53.04 wt. % O, based on the total weight of the catalyst.

In some embodiments, the catalyst has an MCM-22 crystal phase of an MWW-type. Although in certain embodiments, other crystal phases such as mordenite, Kenyaite, and a combination thereof may also be present, with variations in the weight ratio of Si to Al in the aluminosilicate zeolite.

In some embodiments, the catalyst has a relative crystallinity of 50% to 100%, more preferably 55% to 65%, and yet more preferably 59.2%. In another embodiment, the catalyst has a relative crystallinity of about 85-95%, preferably 87-92%, and more preferably about 90.4%. In some embodiments, the catalyst has a relative crystallinity of 70-80%, preferably 72-78%, preferably 74-77%, preferably 76.8%. In some embodiments, the catalyst has a relative crystallinity of about 75-85%, preferably 77-83%, preferably about 80.5%.

In some embodiments, the catalyst has an average crystal size of 10 nm to 30 nm, more preferably 14 to 16 nm, and yet more preferably 15.3 nm. In some embodiments, the catalyst has an average crystal size of about 26-28 nm, preferably 27 nm. In certain other embodiments, the catalyst has an average crystal size of 20-22 nm, preferably about 20.2 nm. In a few other embodiments, the catalyst has an average crystal size of 20-22 nm, preferably about 21.5 nm. In some other embodiments, the catalyst has an average crystal size of about 10 nm.

In some embodiments, the catalyst has a Brunauer-Emmett-Teller (BET) surface area of 400 m$^2$/g to 500 m$^2$/g, more preferably 430 m$^2$/g to 460 m$^2$/g, and yet more preferably 457.5 m$^2$/g. In some embodiments, the catalyst has a BET surface area of about 470-480 m$^2$/g, preferably about 473-477 m$^2$/g, and more preferably about 474.1 m$^2$/g. In certain other embodiments, the catalyst has a BET surface area of 355-365 m$^2$/g, preferably 360-364 m$^2$/g, and more preferably about 363.5 m$^2$/g. In a few other embodiments, the catalyst has a BET surface area of 320-330 m$^2$/g, preferably 322-328 m$^2$/g, preferably about 325.1 m$^2$/g. In some other embodiments, the catalyst has a BET surface area of 230-245 m$^2$/g, preferably about 235-242 m$^2$/g, and more preferably about 239.5 m$^2$/g.

In some embodiments, the catalyst has an external surface area of 100 m$^2$/g to 150 m$^2$/g, more preferably 120 m$^2$/g to 140 m$^2$/g, and yet more preferably 129 m$^2$/g. In some embodiments, the catalyst has an external surface area of 74-75 m$^2$/g, preferably 74.3 m$^2$/g. In some embodiments, the catalyst has an external surface area of 90-110 m$^2$/g, preferably 95-102 m$^2$/g, and more preferably about 98.4 m$^2$/g. In some embodiments, the catalyst has an external surface area of 100-105 m$^2$/g, preferably 102.8 m$^2$/g. In some embodiments, the catalyst has an external surface area of 90-95 m$^2$/g, preferably about 92-94 m$^2$/g, and more preferably 93.5 m$^2$/g.

In some embodiments, the catalyst has an average pore size of 2 nm to 5 nm, more preferably 3 nm to 4 nm, and yet more preferably 3.67 nm. In some embodiments, the catalyst has an average pore size of 2-3 nm, preferably 2.09 nm. In a few other embodiments, the catalyst has an average pore size of 3-4 nm, preferably about 3.05 nm. In certain other embodiments, the catalyst has an average pore size of 4-5 nm, preferably 4.4 nm.

In some embodiments, the catalyst has a mesopore volume of 0.1 cm$^3$/g to 0.3 cm$^3$/g, more preferably 0.2 cm$^3$/g to 0.25 cm$^3$/g, and yet more preferably 0.218 cm$^3$/g; and a micropore volume of 0.01 cm$^3$/g to 0.2 cm$^3$/g, more preferably 0.1 cm$^3$/g to 0.15 cm$^3$/g, and yet more preferably 0.13 cm$^3$/g. In some embodiments, the catalyst has a mesopore volume of 0.05 cm$^3$/g to 0.2 cm$^3$/g, and more preferably about 0.091 cm$^3$/g; and a micropore volume of 0.1 cm$^3$/g to 0.18 cm$^3$/g, and more preferably 0.156 cm$^3$/g. In some embodiments, the catalyst has a mesopore volume of 0.1 cm$^3$/g to 0.2 cm$^3$/g, more preferably 0.15 cm$^3$/g to 0.18 cm$^3$/g, and yet more preferably 0.167 cm$^3$/g; and a micropore volume of 0.01 cm$^3$/g to 0.2 cm$^3$/g, more preferably 0.05 cm$^3$/g to 0.15 cm$^3$/g, and yet more preferably 0.088 cm$^3$/g. In some embodiments, the catalyst has a mesopore volume of 0.1 cm$^3$/g to 0.2 cm$^3$/g, more preferably 0.14 cm$^3$/g to 0.18 cm$^3$/g, and yet more preferably 0.152 cm$^3$/g; and a micropore volume of 0.05 cm$^3$/g to 0.2 cm$^3$/g, more preferably 0.059 cm$^3$/g.

In an embodiment, the catalyst has an acid density of 0.2 milli moles per gram (mmol/g) to 0.6 mmol/g, preferably 0.3-0.5 mmol/g, or about 0.4 mmol/g. As used herein, the term 'acid density' refers to the concentration or strength of an acid solution. More specifically, it denotes the amount of acid sites present in each volume of solution, generally measured in terms of molarity (moles of acid per liter of solution) or normality (equivalents of acid per liter of solution). The acid site density of zeolites can be used to describe the complexity of catalytic reactions over them.

According to a second aspect of the present disclosure, a method of cracking a hydrocarbon is described. The method includes contacting the hydrocarbon with the catalyst at a temperature of 200° C. to 600° C., preferably 300-500° C., 300-400° C. more preferably 350° C. in a reactor. The reactor is at least one of a fixed-bed reactor, a trickle-bed reactor, a moving bed reactor, a rotating bed reactor, a fluidized bed reactor, and a slurry reactor. In a preferred embodiment, the reactor is a fixed-bed reactor.

In some embodiments, the hydrocarbon has 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms. In some embodiments, the hydrocarbon has 5 to 20 carbon atoms. In some embodiments, the hydrocarbon may include, but is not limited to, pentane, hexane, heptane, octane, nonane, decane, undecane, dodecane, tridecane, tetradecane, pentadecane, hexadecane, heptadecane: octadecane, nonadecane, eicosane. In a preferred embodiment, the hydrocarbon is n-dodecane.

Catalytic cracking of a hydrocarbon, particularly n-dodecane, with the catalyst of the present disclosure yields one or more compounds. Each of these one or more compounds has carbon atoms less than/smaller carbon atoms than the hydrocarbon. For example, if the hydrocarbon is n-dodecane, catalytic cracking results in yielding two or more compounds having less than 10 atoms, like 1, 2, 3, 4, 5, 6, 7, 8, and 9 carbon atoms. Some portion of the hydrocarbon that does not react with the catalyst is referred to as an unreacted hydrocarbon. The unreacted hydrocarbon may be contacted again with the catalyst for the catalytic cracking process.

The catalyst has a conversion rate of at least 90% to the plurality of compounds, in other words, at least 90% of the hydrocarbon is converted to compounds having a smaller number of carbon atoms than the hydrocarbon, with the catalyst of the present disclosure. In a preferred embodiment, the compound(s) have about 1-6 carbon atoms, preferably 2-5 carbon atoms. In some embodiments, the compound(s) include at least one of olefins and/or paraffins. In a preferred embodiment, the compounds include both olefins and paraffins. The percentage of paraffins to olefins in the compounds is in the range of 1:1 to 2:1, preferably 1:1 to 1:1.5. The paraffin may be linear or branched, together referred to as total paraffin/paraffin. In some embodiments, the compounds include at least 30% linear paraffin, preferably 35% linear paraffin.

In a specific embodiment, when the catalyst has a weight ratio of $SiO_2$ to $Al_2O_3$ is 28.8:1 and the hydrocarbon is n-dodecane, at least 99.9% of n-dodecane is converted to two or more compounds, each having carbon atoms smaller/lesser than n-dodecane, with the catalyst. The compounds include at least 25% of paraffins having 3-4 carbon atoms, preferably propane and butane; and at least 15% of olefins 2-4 having carbon atoms, preferably ethylene and propylene.

While not wishing to be bound to a single theory, it is thought that variations in the weight ratio of $SiO_2$ to $Al_2O_3$ in the catalyst produce a synergistic combination of properties which result in improved catalysis. When the catalyst has a weight ratio of $SiO_2$ to $Al_2O_3$ is 28.8:1 no crystal impurities of mordenite or kenyaite are observed and a high surface area flake morphology is observed. In addition, a high micro and meso pore volume is observed. This results in an increase the availability of active sites during catalysis which can be accessed by large hydrocarbons such as n-dodecane.

EXAMPLES

The following examples demonstrate a method of cracking hydrocarbons. They are provided solely for illustration and are not to be construed as limitations of the present disclosure, as many variations are possible without departing from the spirit and scope of the present disclosure.

Example 1: Materials and Chemicals

LUDOX® colloidal silica HS-40 $SiO_2$, 40 percent by weight (wt. %), sodium hydroxide (NaOH) pellets for analysis 99 wt. %, technical sodium aluminate anhydrous ($Al_2O_3$) 50% to 56%, $Na_2O$ 37% to 45%, hexamethyleneimine (HMI) ≥98 wt. % were obtained from Merck. Further, distilled water from Milli-Q water purification, ammonium nitrate ($NH_4NO_3$) ACS reagent, ≥98 wt. % were obtained from Merck.

Example 2: Preparation of High Silica MCM-22 (Base Model Zeolite)

Starting with 0.6 g of NaOH diluted in 54 g of distilled water to produce a high silica content ($SiO_2/Al_2O_{3=56.6}$). After the alkali solution had been made, 22.5 g of colloidal silica was added, and the mixture was stirred until it was uniform. As a result, 5.9 ml of HMI was added dropwise, and the mixture was continued for approximately 10 minutes (min). After that, 0.482 g of sodium aluminate powder was slowly added while the nucleation age was allowed to continue for 24 hours (h) at a minimum mixing speed of 350 revolutions per minute (rpm). The final molar composition of the mixture of the parent was 56.6 $SiO_2$: 1.0 $Al_2O_3$: 1.1 $Na_2O$: 5.7 NaOH: 22.5 HMI: 1416.5$H_2O$. This solution was then put into Teflon-lined, covered by a steel autoclave under fixed rotation of 60 rpm within the KH 02 hydrothermal synthesis units from Japan at 150° C. for seven days. After that, the autoclave was submerged in a waterbed to halt the crystallization process and quench. Further, the resulting mixture was cleaned with deionized water, dried at 100° C. to remove surplus, and calcined at 550° C. for at least 5 h to remove leftover HMI templates. Furthermore, each gram of calcined catalyst was mixed with 20 milliliters (mL) of $NH_4NO_3$ and heated to 70° C. with constant stirring for at least an hour. Moreover, the catalyst was subjected to a second purification process. This last catalyst already existed in the H form and was ready to be examined.

Example 3: Synthesis of MCM-22 with Different $SiO_2/Al_2O_3$ Ratios

MCM-22 with different $SiO_2/Al_2O_3$ ratios were synthesized by varying the amount of colloidal silica and fixing the weight of sodium aluminate and the remaining chemical precursors. In an example, to discover the effect of silica content, the amount of colloidal silica has ranged from one-third (7.5 g), half (11.25 g), doubled (45 g), to tripled (67.5 g), from the base model MCM-22. Further, the variations were denoted as Si0.33, Si0.5, Si2, and Si3, respectively. The molar composition of the initial gel mixture for each experiment of these studies is listed in Table 1.

TABLE 1

The molar composition of the initial gel mixture of the sample experiment.

| Samples | $SiO_2$ | : | $Al_2O_3$ | : | $Na_2O$ | : | NaOH | : | $H_2O$ | : | HMI |
|---|---|---|---|---|---|---|---|---|---|---|---|
| Si0.33 | 18.9 | : | 1.0 | : | 1.1 | : | 5.7 | : | 1416.5 | : | 22.5 |
| Si0.5 | 28.8 | : | 1.0 | : | 1.1 | : | 5.7 | : | 1416.5 | : | 22.5 |
| MCM-22 | 56.6 | : | 1.0 | : | 1.1 | : | 5.7 | : | 1416.5 | : | 22.5 |
| Si2 | 112.2 | : | 1.0 | : | 1.1 | : | 5.7 | : | 1416.5 | : | 22.5 |
| Si3 | 169.9 | : | 1.0 | : | 1.1 | : | 5.7 | : | 1416.5 | : | 22.5 |

Example 4: Characterization Techniques

MCM-22 zeolite phase was analyzed using several methods, including powder X-ray diffraction (P-XRD) using Rigaku Miniflex II diffractometer equipped with Cu Kα radiation ( ) 0.15406) and 600 watts (W) X-ray source. The observation was conducted upon 2θ angle ranging from 5° to 50°, a scan speed of 3°/min, and a step size of 0.02°, The relative crystallinity was determined using the following equation:

Relative crystallinity =

$$\frac{\text{Total area under the peak of specified sample}}{\text{Total area under the peak of reference sample}} \times 100$$

Scanning electron microscopy (SEM) was analyzed with FESEM/FIB/GIS Tesca Lyra-3 machines. About 0.1 g of each final sample was taken and diluted with ethanol. Further, the samples were shaken to provide even particle dispersion upon the alumina holder covered by copper tape (preferably double-sided). Prepared distributed particle sample upon holder then coated by gold using plasma machine for about 30 s before analysis. Nitrogen ($N_2$) adsorption and desorption isotherm were performed using an accelerated surface area and porosimeter system (ASAP™-2020) by Micromeritics with a liquid $N_2$ probe from Linde. Each sample analyzed was evacuated at 550° C. for at least 3 h and then outgassed at 300° C. for under 6 h.

Brunauer-Emmett-Teller (BET) methods were performed to determine the surface area properties of materials. In contrast, size particle distribution was calculated via the Barret-Joyner-Halenda (BJH) model and micropore volume was obtained using the t-plot method. Temperature-programmed desorption (TPD) of ammonia ($NH_3$) probe was conducted to check the amount of acid density of each variation sample using BELCAT II, MicrotracBEL Corp catalyst analyzer equipped with thermal conductivity detector (TCD). Pyridine adsorption was used to test the acidity of the catalysts. A NICOLET 6700 FTIR with an MCT detector was used for the pyridine adsorption. The zeolite samples were processed in a vacuum at 550° C. for 1 h before being put in a ZnSe cell. After the piece was cooled to 150° C., pyridine was added for 10 min as a probe molecule and removed under a vacuum at the same temperature.

Example 5: Catalytic Performance for n-Dodecane Cracking to Olefins Measurements The catalytic evaluation was carried out in a fixed-bed reactor, as illustrated in FIG. 1. Before the reaction, 0.3 g of prepared H-form catalyst was sieved into 300 mm mesh particle and placed within a quartz column reactor. The catalyst was outgassed under $N_2$ with a flow rate of 30 cubic centimeters per minute ($cm^3$/min) for 1 h and used as a gas carrier during the reaction outgassed at a temperature of 550° C. for 30 min before the catalytic performance. N-dodecane and $N_2$ were pumped into the reactor at 16 milliliters per second (mL/s). The reaction was conducted at a temperature of 350° C. for 120 min. Further, the effluent was sent to a cold trap (−10° C.) to separate the liquid and gas fractions. The gas was sent directly from the cold trap to a gas chromatographer (GC), Shimadzu 2030. Gases products were analyzed by GC to determine paraffin and olefin yield. In contrast, liquid products were analyzed by GC Shimadzu 2014 to observe the composition of unreacted feed. Both machines were attached with flame indicator detector (FID) and PIONA analysis to quantify the amount of converted feed and selectivity of the products. The conversion of n-dodecane feed (X) was defined as the number of moles of n-dodecane reacted per mole of n-dodecane fed. Conversion, selectivity, and yield were measured by equations as follows:

$$\text{Conversion}(x) = \frac{(\text{Moles N-dodecane reacted})}{(\text{Moles of N-dodecane fed})} \times 100\%$$

whereas selectivity(S) and yield (Y) were determined as equal to the ratio of desired products to undesired products and how much of the desired product was formed, respectively.

$$\text{Selectivity}(S) = \frac{(\text{Total desired moles product})}{(\text{Total undesired moles product})} \times 100\%$$

$$\text{Yield}(Y) = \frac{(\text{Desired moles product})}{(\text{n-dodecane feed moles consumption})} \times 100\%$$

Example 6: Physiochemical Properties of MCM-22

Figure 2:
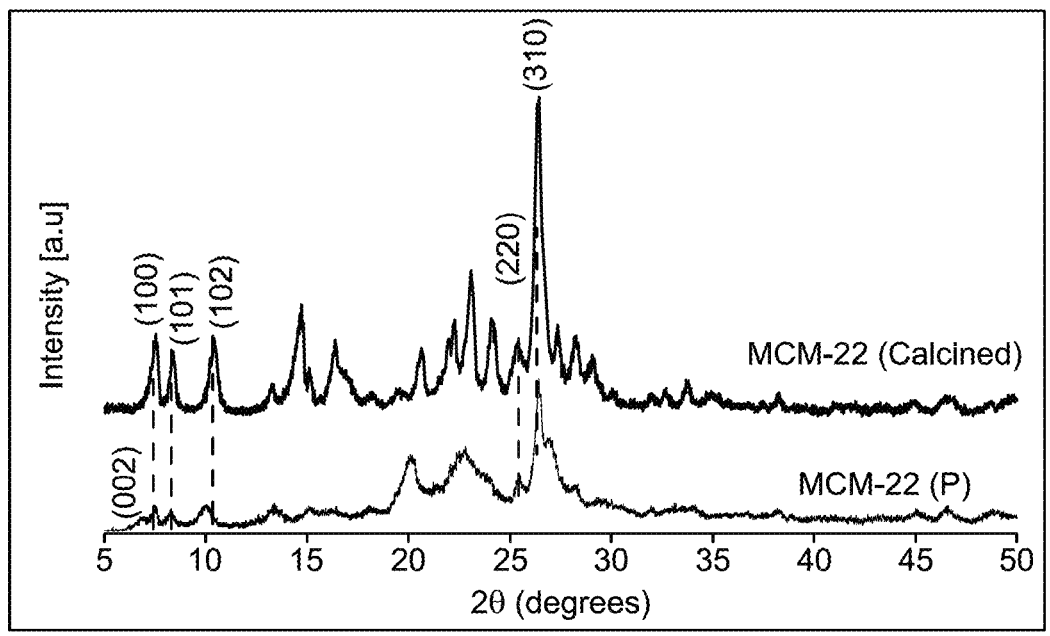
FIG. 2 depicts X-ray diffraction (XRD) patterns of high-silica MCM-22 before and after calcination, according to certain embodiments.

FIG. 2 illustrates XRD patterns of high-silica MCM-22 before and after calcination (parent or H-form). As can be seen from FIG. 2, both samples exhibit five peaks that correlate to the MCM-22. The parent sample MCM-22 shows a single peak of (002) planes at a 6.6° angle, indicating an ordered layered (intra-layer) structure with a d-spacing of roughly 2.4 nm. Following calcination, this single peak of (002) disappeared after taking out the structure-directing agent HMI as an organic template. Furthermore, the ordered layered remains and build a 3D framework that includes interlayer and intralayer structures. The intra-layered gap between the sheets corresponded to the (100) plane at a 7° angle with a d-spacing of 1.2 nm. Meanwhile, the interlayered space reflects the (102) plane at a 10° angle, representing the distance between the cups that repeated along the b-axis. The intra-layered spacing shrunk by half due to the condensation of crystal structure during the calcination process where the space has been previously filled by HMI. Consequently, this lamellae structure of MCM-22 was a MWW phase zeolite compared to other zeolitic materials.

Example 7: Effect of $SiO_2/Al_2O_3$ Ratio on MCM-22

The effect of the $SiO_2/Al_2O_3$ ratio on MCM-22 was investigated, and Table 2 displays the elemental composition of MCM-22 with varying $SiO_2/Al_2O_3$ ratios. The initial gel compositions were altered by reducing/increasing the silicon source; however, the percentage of silicon atoms in all samples remained the same. Further, the number of aluminum atoms decreased as the sample was changed from Si0.33 to Si3. Consistent with the composition of the original gel, this phenomenon causes the $SiO_2/Al_2O_3$ ratio to rise in an ascending pattern. Accordingly, the difference between the Si/Al ratio of H-form catalysts, as shown in Table 2, with initial gel composition, as shown in Table 1, is caused by the post-treatment process of dealumination with $NH_4NO_3$.

Figure 3:
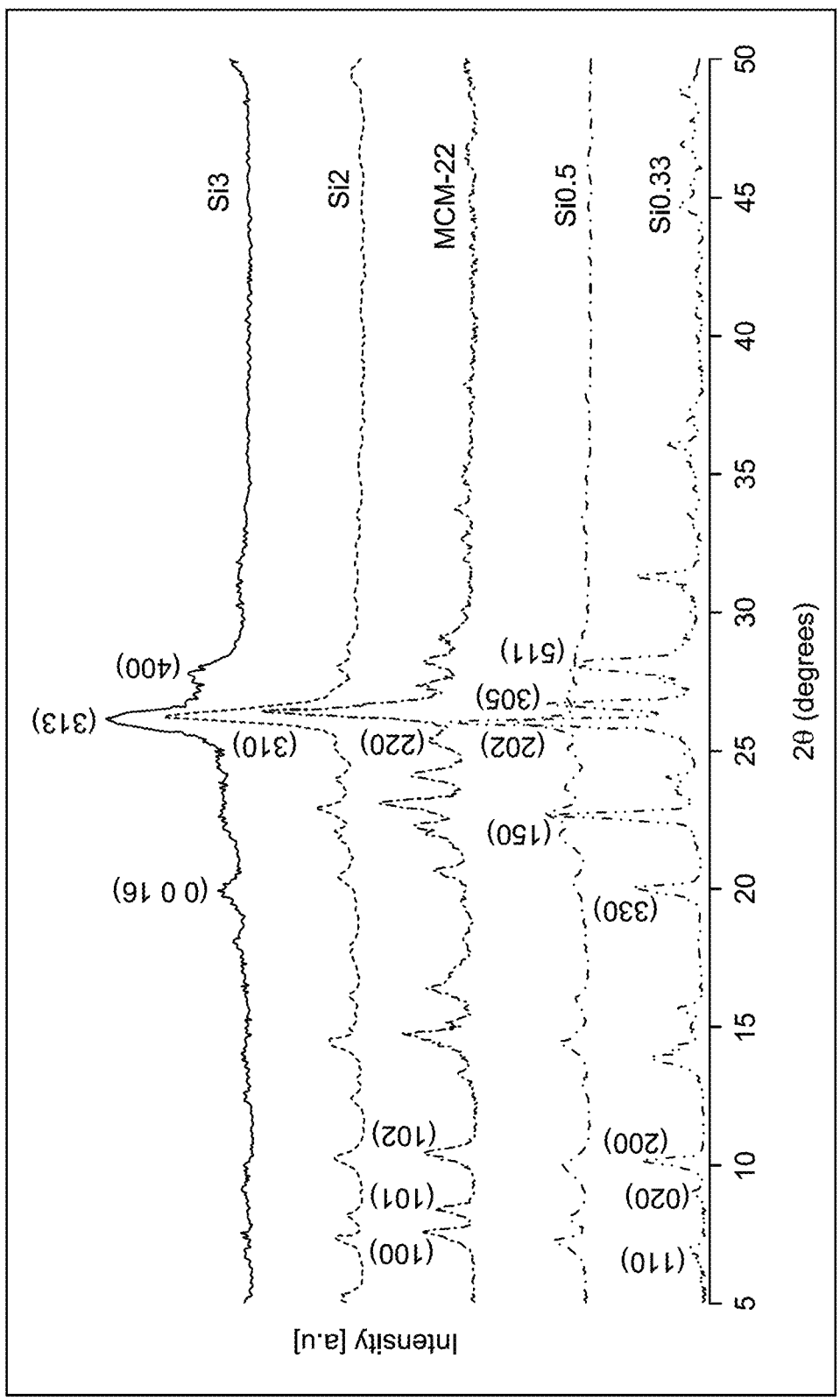
FIG. 3 shows XRD patterns of MCM-22 with different $SiO_2/Al_2O_3$ ratios, according to certain embodiments.

FIG. 3 shows the detailed crystal structure transformation within the samples with different $SiO_2/Al_2O_3$ ratios. At a low $SiO_2/Al_2O_3$ ratio (Si0.33), the corresponding peaks show a distinguish phase from the initial MCM-22, which represents the mordenite (MOR) phase. The 2θ peaks of MOR for Si0.33 including at 10.16°, 19.98°, 22.62°, 26.01°, 26.65°, and 28.15° which corresponds to the (200), (330), (150), (202), (305), (511) planes respectively. These peaks align with JCPDS card no. 43-0171, AMCSD no. 0003444, and inorganic crystal structure database (ICSD).

Table 3 shows a complete list of the effect of the $SiO_2/Al_2O_3$ ratio on the crystal phase of the MWW family. The experiments obtained MCM-22 with a high silica-alumina ratio content at 56.6 with good crystallinity compared to previous material fabricated with less silica content, unlike sample Si0.5 with $SiO_2/Al_2O_3$ ~30 possessed a complete MWW zeolite phase. Further, this sample has lower relative crystallinity than the high-silica base model MCM-22 ($SiO_2/Al_2O_3$=56.6). This is due to peak reduction at the same 2θ angle, including 7.6°, 8.4°, 10.4°, 25.3°, and 26.3°, which corresponds to (100), (101), (102), (220) and (310) planes. Furthermore, sample Si2 with $SiO_2/Al_2O_3$ ~113 possessed similar peaks with zeolite MWW phase but with a high intensity on 2θ angle of about 26°. This peak was ascribed to several planes involving (310) for the MWW phase and (313) for Kenyaite, which overlapped each other. The broadening of the diffraction peak signifies defects in the stacking mode and crystal structure and reduced crystal size. Additionally, sample Si3 only shows two peaks at 2 angles, 26.1° and 27.6°, which is associated with the (313) and (400) planes. The planes also occurred on the synthetic phase zeolite of Kenyaite. In addition, the broad range observation, as listed in Table 3, from the lowest silica content (Si0.33) to the highest silica content (Si3) proves that the pure MWW phase has a limited crystal window of $SiO_2/Al_2O_3$ ratio between ca. of about 25 to 100, as depicted in FIG. 4.

Figure 4:
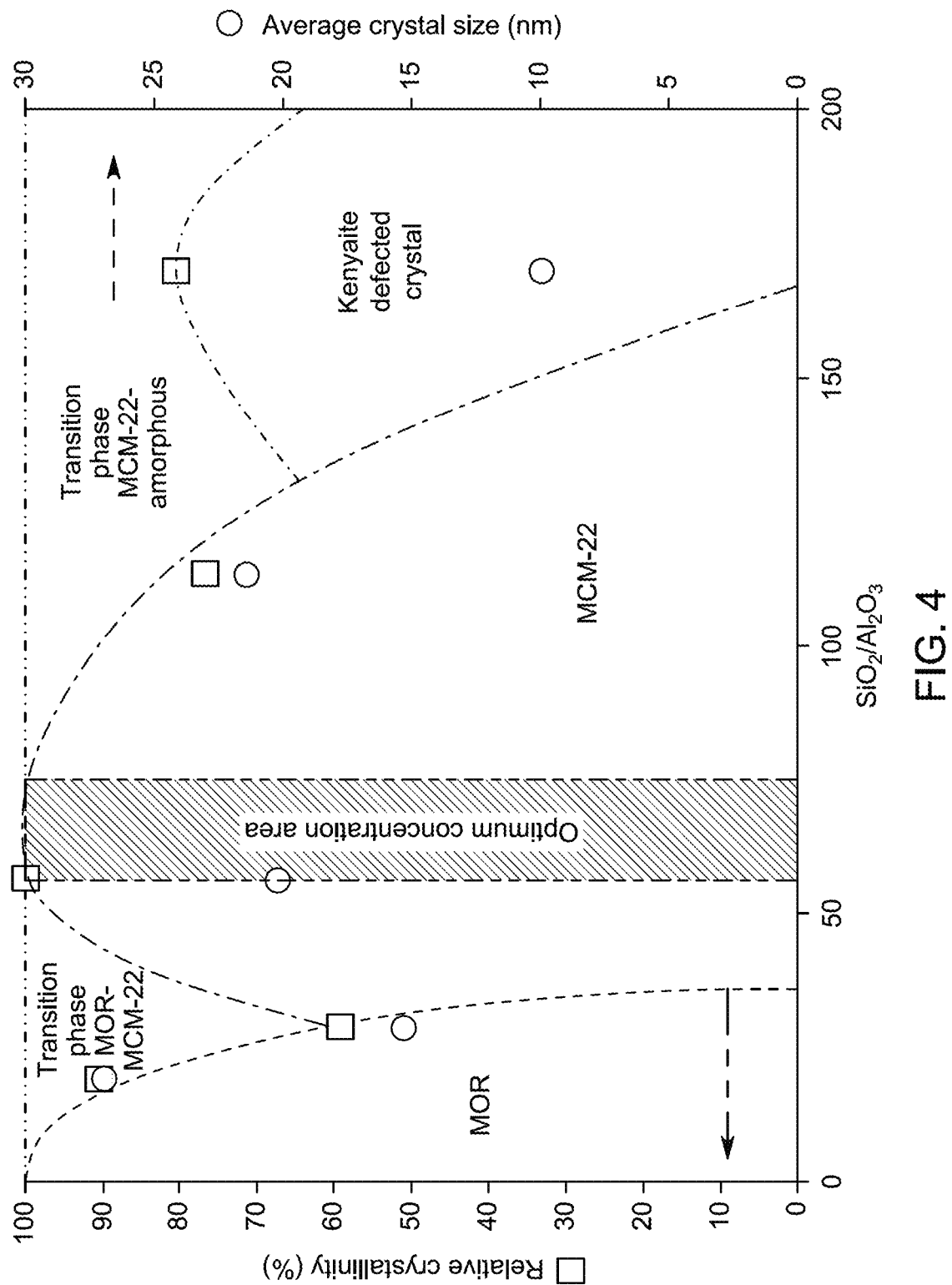
FIG. 4 shows possible transformations of zeolite MCM-22 with different $SiO_2/Al_2O_3$ ratios, according to certain embodiments.

Thus, several impurities phases such as MFI, Kenyaite, or MOR may occur from the final product of zeolite with relative crystallinity ranging from ca. 59% to 100%, as shown in FIG. 4. The average crystal size of this zeolite was from 15 to 27 nm, as shown in FIG. 4. The defective materials established a smaller average crystal size due to the phase that nearly became amorphous.

TABLE 2

Elemental analysis of MCM-22 with different $SiO_2/Al_2O_3$.

| Name | Si (wt. %) | Al (wt. %) | O (wt. %) | Trace element (wt. %) | Si/Al |
|---|---|---|---|---|---|
| Si 0.33 | 43.56 | 3.58 | 52.85 | 0.47 | 12.18 |
| Si 0.5 | 45.02 | 1.95 | 53.04 | 0.43 | 23.11 |
| MCM-22 | 46.12 | 0.69 | 53.18 | 0.44 | 66.55 |
| Si2 | 45.78 | 0.37 | 53.24 | 0.54 | 125.41 |
| Si3 | 46.53 | 0.24 | 53.24 | 0.39 | 193.13 |

TABLE 3

A comprehensive list of the consequences of the $SiO_2/Al_2O_3$ ratio on the MWW crystal phase.

| Samples | $SiO_2/Al_2O_3$ | Relative Crystallinity (%) | Average crystal size (nm) | Crystal phase |
|---|---|---|---|---|
| Si 0.33 | 18.9 | 90.4 | 27.0 | MOR |
| Si 0.5 | 28.8 | 59.2 | 15.3 | MCM-22 |
| MCM-22 | 56.6 | 100.0 | 20.2 | MCM-22 |
| Si2 | 113.2 | 76.8 | 21.5 | Kenyaite |
| Si3 | 169.8 | 80.5 | 10.0 | Kenyaite (defected) |

Example 8: SEM Analysis

Figure 5A:
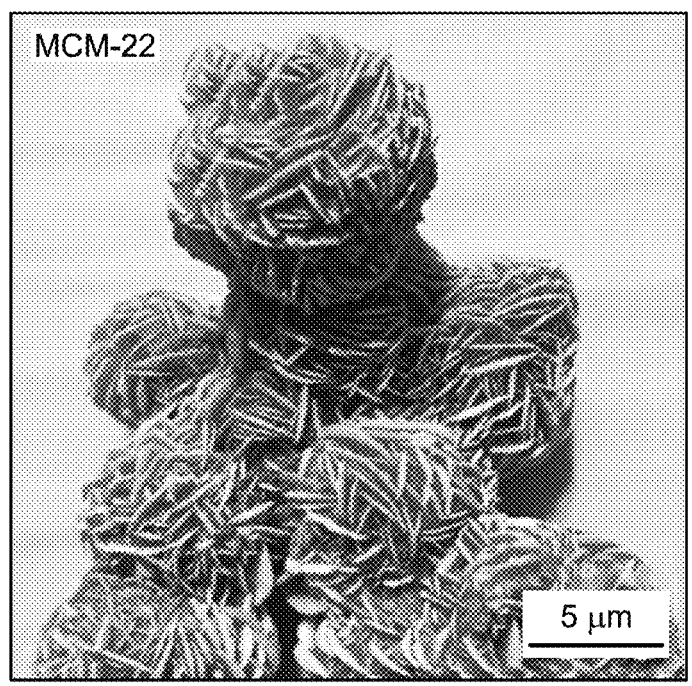
FIG. 5A is a scanning electron microscopy (SEM) image depicting the morphology of MCM-22 at a magnification of 5 micrometers (μm), according to certain embodiments.
Figure 5B:
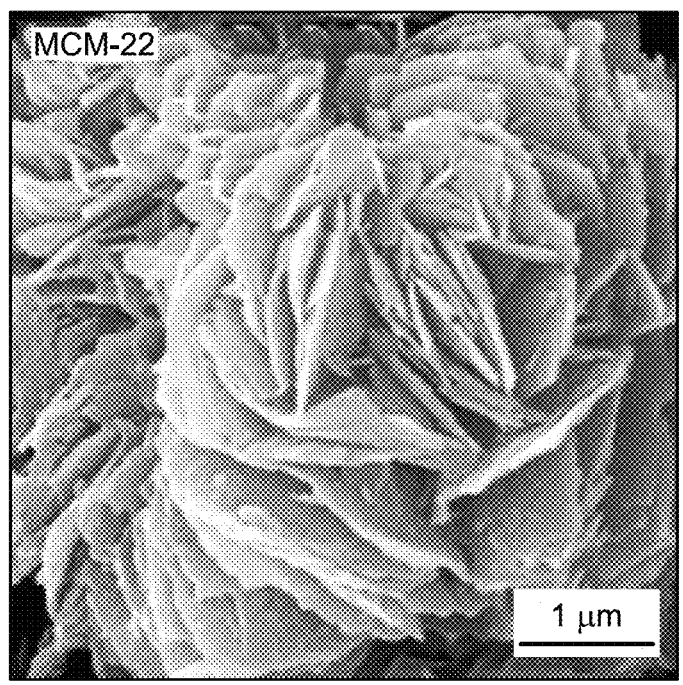
FIG. 5B is an SEM image depicting the morphology of MCM-22 at a magnification of 1 μm, according to certain embodiments.
Figure 5C:
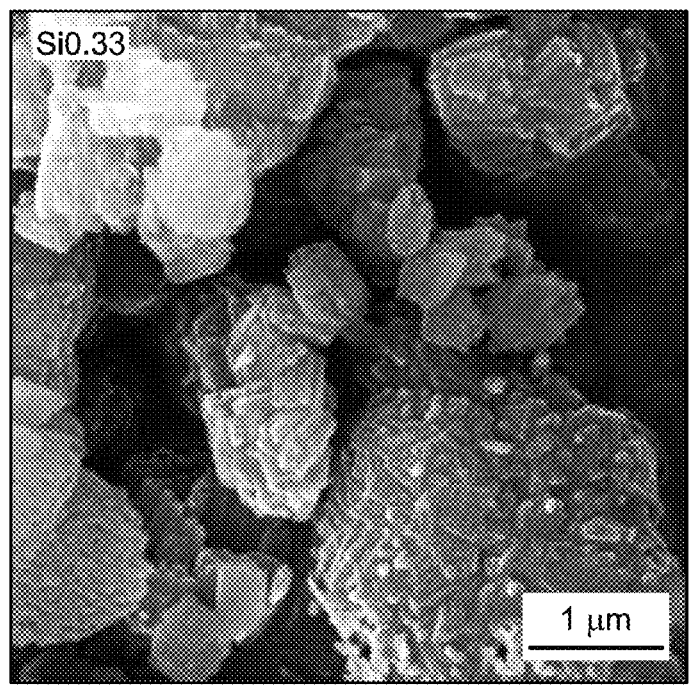
FIG. 5C is an SEM image depicting the morphology of Si0.33, according to certain embodiments.
Figure 5D:
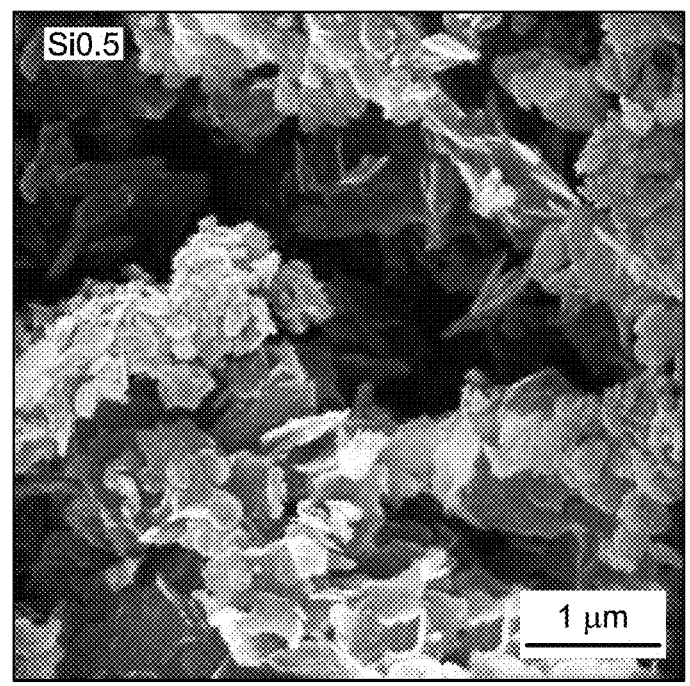
FIG. 5D is an SEM image depicting the morphology of Si0.5, according to certain embodiments.
Figure 5E:
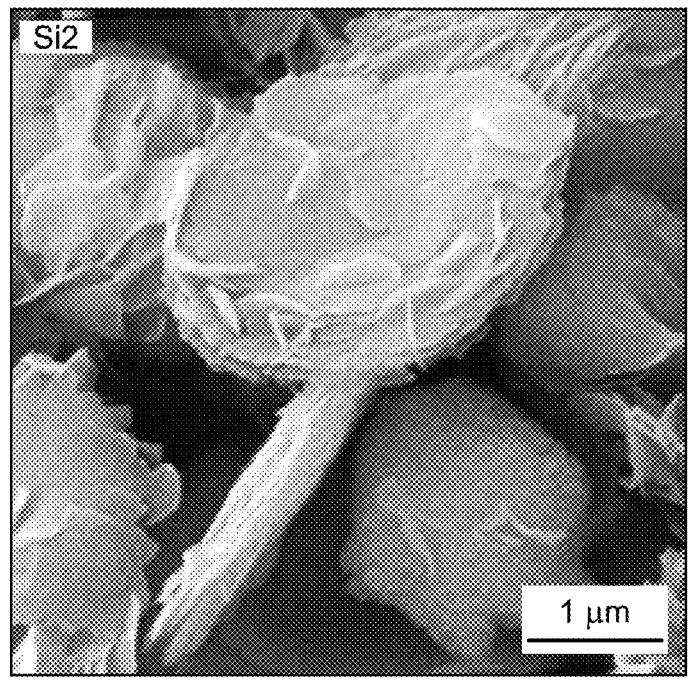
FIG. 5E is an SEM image depicting the morphology of Si2, according to certain embodiments.
Figure 5F:
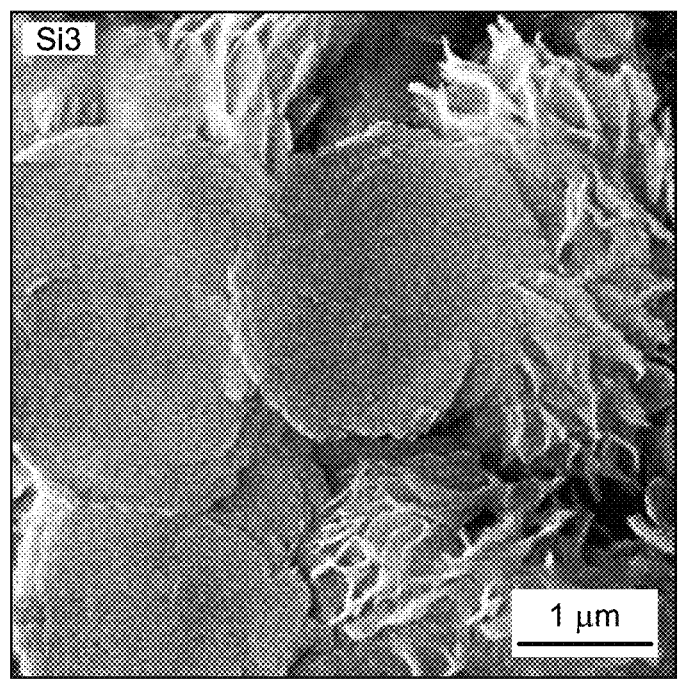
FIG. 5F is an SEM image depicting the morphology of Si3, according to certain embodiments.

SEM analysis was carried out to investigate the morphology as shown in FIGS. 5A-5F. MCM-22 has a structure stacked on the c-axis and simultaneously had an intergrowth along the b-axis as shown in FIGS. 5A-5B. Further, FIGS. 5C-5F depicts a different morphology of MCM-22 with various $SiO_2/Al_2O_3$ ratios that support diffractogram data in FIG. 3. As can be seen from FIG. 5C, the sample Si0.33 ($SiO_2/Al_2O_3$ ~19) has a parallelepipedal configuration stacked and joined together to build a more considerable crystal mordenite phase structure, as seen in FIG. 5D, sample Si0.5 ($SiO_2/Al_2O_3$ ~28.8) showed a MWW phase with a bran or flake shape in a stacking mode. Furthermore, as can be seen from FIGS. 5E-5F, high silica zeolite MCM-22 (Si2 and Si3) occurred as a 'flowery shape like' obtained when synthesizing synthetic Kenyaite. In addition, at high $SiO_2/Al_2O_3$ ~169, the phase achieves more than 80% phase Kenyaite. Based on the SEM findings, there is a definite change in different structural phases of zeolite beginning with MOR when the $SiO_2/Al_2O_3$ ratio is low (Si0.33) with prismatic-hexagon morphology. It starts to build a Bran-like crystal with small particles (Si0.5) before it grows into a rosette-like structure, as in the MCM-22, Si2, and Si3 samples.

Figure 6:
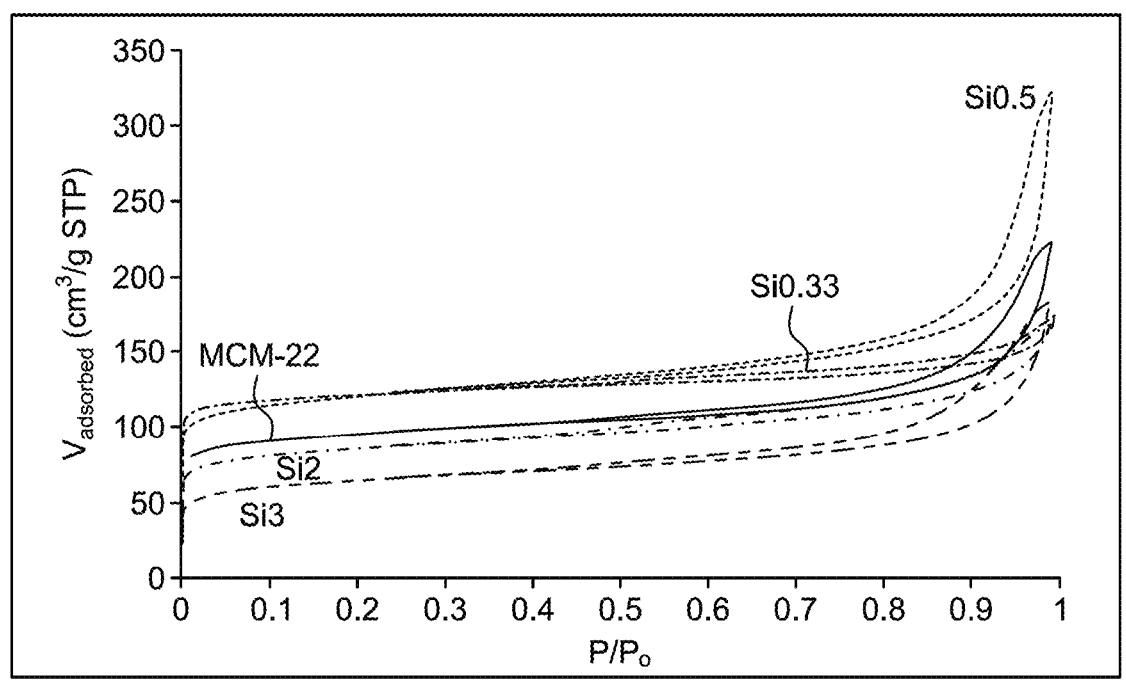
FIG. 6 depicts nitrogen physisorption-desorption of MCM-22 with different $SiO_2/Al_2O_3$ ratios, according to certain embodiments.

Example 9: Nitrogen Physisorption-Desorption $N_2$ physisorption-desorption analysis was performed to investigate textural characteristics and pore size distribution of MCM-22 with varied $SiO_2/Al_2O_3$ ratios; corresponding results are shown in FIG. 6 and Table 4. All sample variants have isotherms of type IV, complete with hysteresis loops between the adsorption and desorption of $N_2$, as shown in FIG. 6, indicating the material has mesoporous and microporous features within its structure. Base model MCM-22 with $SiO_2/Al_2O_3$~56.6 has a total BET surface area of 363.5 $m^2/g$ with a total pore volume of 0.224 $cm^3/g$. Modifying silica content affects the crystal framework, leading to differences in its textural properties.

TABLE 4

Textural properties of MCM-22 with different $SiO_2/Al_2O_3$ ratios

| Samples | $S_{BET}$ ($m^2/g$) | $S_{ext}$ ($m^2/g$) | $S_{micro}$ ($m^2/g$) | $V_{micro}$ ($cm^3/g$) | $V_{meso}$ ($cm^3/g$) | Average adsorption pore width (nm) |
|---|---|---|---|---|---|---|
| Si0.33 | 474.1 | 74.3 | 399.8 | 0.156 | 0.091 | 2.09 |
| Si0.5 | 457.5 | 129.0 | 328.5 | 0.130 | 0.218 | 3.67 |
| MCM-22 | 363.5 | 98.4 | 265.1 | 0.105 | 0.119 | 3.43 |
| Si2 | 325.1 | 102.8 | 222.3 | 0.088 | 0.167 | 3.05 |
| Si3 | 239.5 | 93.5 | 146.6 | 0.059 | 0.152 | 4.40 |

For example, sample Si0.33, which has a mordenite phase, has a total BET surface area of 474.1 $m^2/g$ with a total pore volume of 0.247 $cm^3/g$, higher than the base model MCM-22, whereas samples with high silica content, such as Si3, have lower total BET surface area (239.5 $m^2/g$) and total pore volume (0.211 $cm^2/g$) compared to the base model MCM-22. Furthermore, sample Si0.5 has a higher external surface area (Sext) compared to other samples (up to ca. 130 $m^2/g$) caused by a smaller particle with an average crystal size of around 15 nm. Conversely, for the base model MCM-22 and the higher $SiO_2/Al_2O_3$ ratio sample, there are no changes in their external surface area, and the capacity obtained is approximately 100 $m^2/g$. However, this decline in BET surface area was attributed to a decrease in the number of microporous surfaces present inside the zeolite structure, as shown in Table 4. The sample Si0.33 has the highest microporous surface area of about ca. 400 $m^2/g$. These results demonstrate that the MOR phase zeolite contains more microporous sites inside its framework than the MWW phase zeolite. Furthermore, the sample Si0.33 has the least external surface area of about 74 $m^2/g$, indicating that the MOR phase surface is less porous than other samples. The decrease in the BET surface area was attributed to the zeolite structure containing fewer microporous surfaces. A sample of MCM-22 with a distinct $SiO_2/Al_2O_3$ ratio may be ordered according to total BET surface area as follows: Si0.33>Si0.5>MCM-22>Si2>Si3, whereas the order of their total pores volume may be sorted as follows: Si0.5>MCM-22>Si0.33>Si3>Si2.

Example 10: Acid Density and Acid Site Distributions

Figure 7:
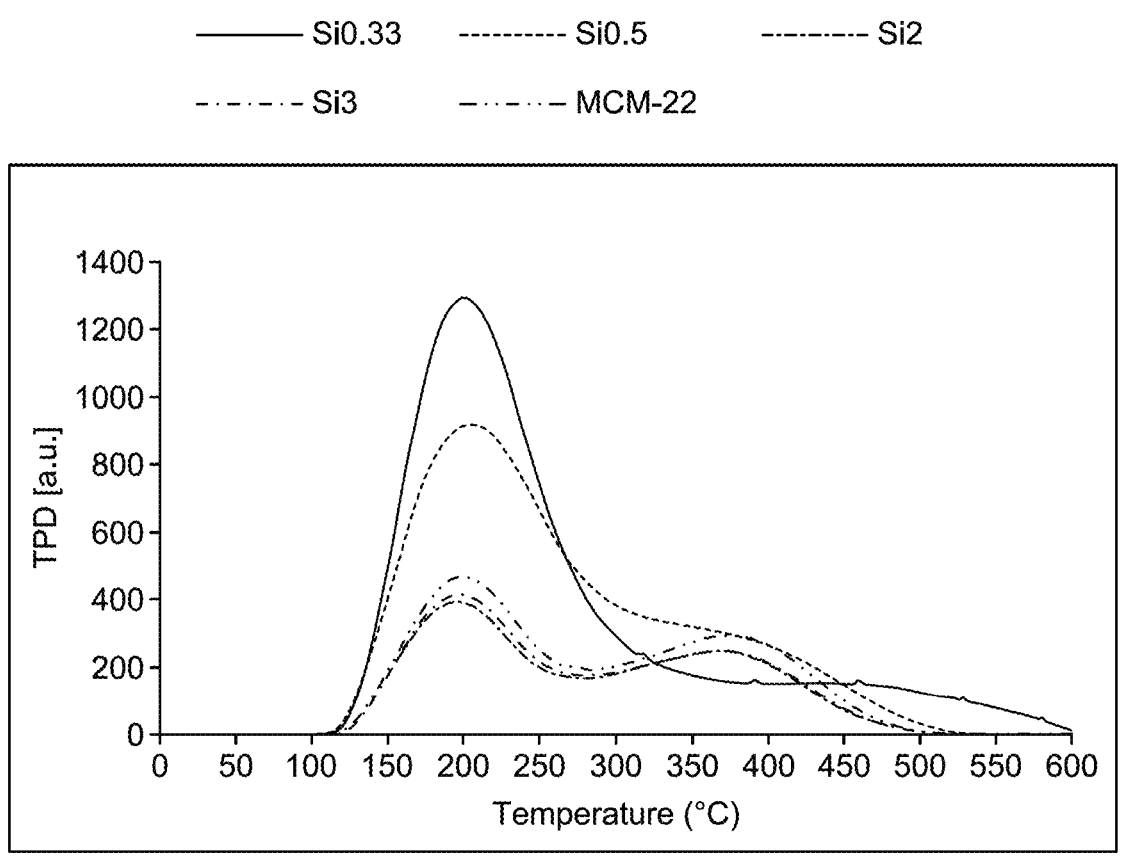
FIG. 7 depicts temperature-programmed desorption (TPD) test results for acid density, according to certain embodiments.
Figure 8:
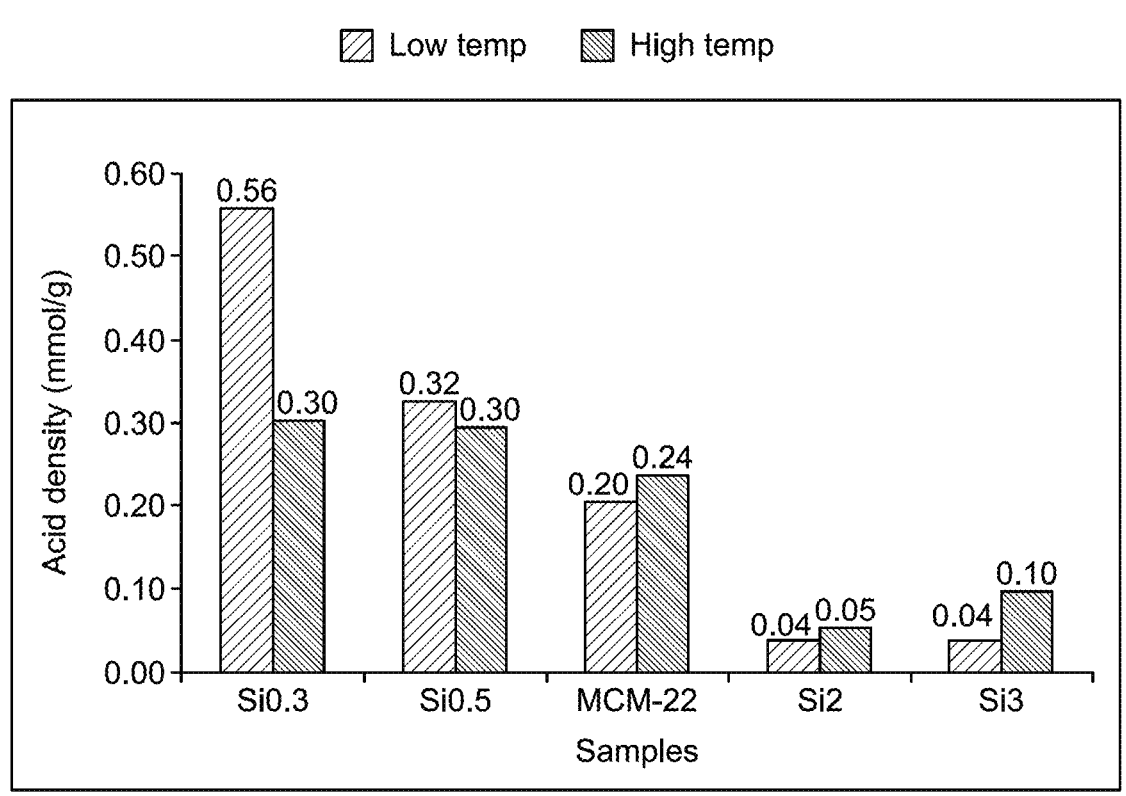
FIG. 8 is a graph depicting the effect of silica concentration on acid density at low and high temperatures, according to certain embodiments.

Using $NH_3$ probes, a TPD examination was carried out to check the quantity of low-temperature acid density (LTAD) and high-temperature acid density (HTAD), as shown in FIG. 7. The base model MCM-22 had an equal acid density at low and high temperatures of 0.20 mmol/g and 0.24 mmol/g, respectively. There was a change of acid density at low temperatures for Si/Al lower than the base model MCM-22 experimented with ($SiO_2/Al_2O_3$=~56.6). The acid density shifted to a higher temperature and reached the highest intensity peaks at 205.1° C. (sample Si0.5), whereas the sample with a higher $SiO_2/Al_2O_3$ than the base model MCM-22 has a decreasing trend and achieves its lowest point at a temperature of 186.1° C. (sample Si3). In addition, the sample Si0.33, which contained the MOR phase, achieved a value of 0.56 mmol/g, the greatest acid density found at a low temperature. Thus, increasing the amount of silica content (higher $SiO_2/Al_2O_3$ ratio) may reduce acid density at low and high temperatures, as shown in FIG. 8.

The sample Si0.5 has better values for both low-temperature and high-temperature acid density for the MWW phase compared to the base model MCM-22. Higher BET surface area and volumetric adsorption (total pore volume) may increase the availability of an unoccupied and probability of getting ion-exchanged with hydrogen donors from acid solutions. Further, the amount of acid density mainly depends on the ion exchange process or method. Furthermore, it may be deduced that the acid density may be ordered from highest to lowest peaks as follows: Si0.33>Si0.5>MCM-22>Si3>Si2.

Figure 9:
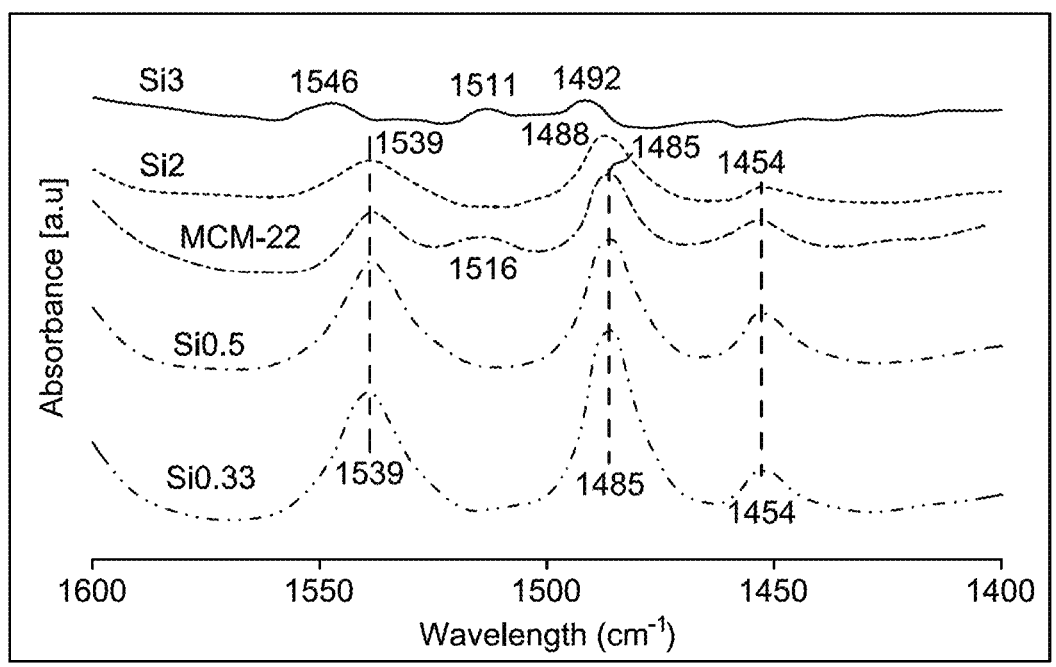
FIG. 9 depicts pyridine adsorption of MCM-22 with different $SiO_2/Al_2O_3$ ratios, according to certain embodiments.

Acid site distribution for the Lewis and Brønsted types is depicted in FIG. 9. The amount of Brønsted acid and Lewis acid sites increased as the silica content went lower (represented at band 1539 cm-1 for BAS and 1454 cm-1 for LAS, respectively).

The above findings demonstrate that a parent gel solution with a low silica concentration (low $SiO_2/Al_2O_3$ ratio) formed extra aluminum atoms within the zeolite framework. The amount of extra framework was also caused by dealumination during the ion exchange process. In contrast, pyridine adsorption (Py-ads) for both BAS and LAS on the sample Si3 was the weakest compared to other samples, indicating the less-defined structure and textural properties of layered zeolite substantially affect its chemical properties. FIG. 9 depicts the following order for BAS and LAS: Si0.33>Si0.5>MCM-22>Si2>Si3.

Example 11: Nuclear Magnetic Resonance (NMR) Spectroscopy

Figure 10:
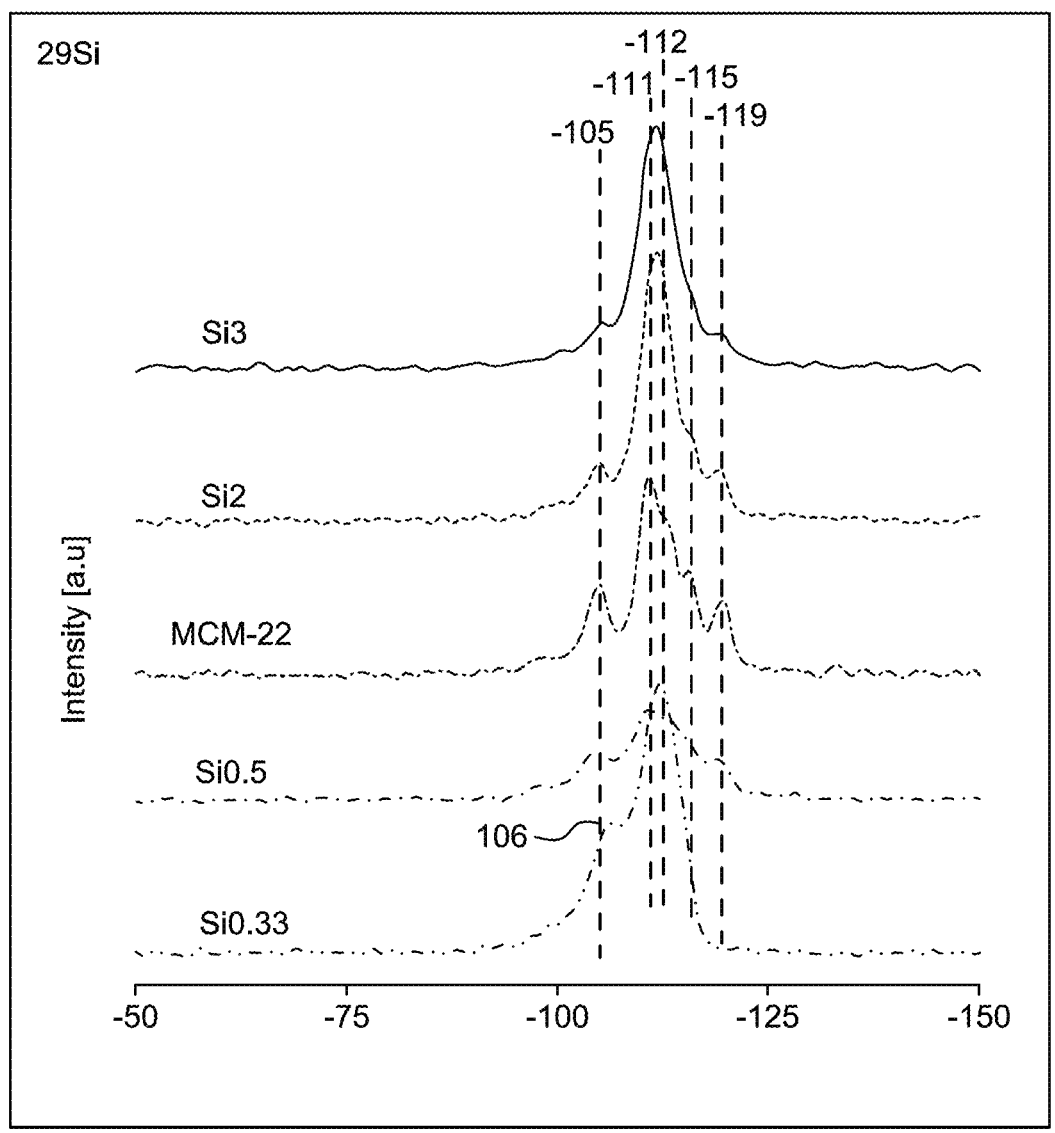
FIG. 10 shows $^{29}Si$ nuclear magnetic resonance (NMR) analysis for MCM-22 with different $SiO_2/Al_2O_3$ ratios, according to certain embodiments.

Referring to FIG. 10, the results of a 29Si NMR study conducted on MCM-22 zeolite with various $SiO_2/Al_2O_3$ ratios are illustrated. In the base model of MCM-22, the spectrum displays at least five chemical shift peaks centered at −105 ppm, −110 ppm, −112 ppm, −115 ppm, and −119 ppm. These peaks correspond to the initial T-coordinated atoms of Si(nAl) and Si(OSi4) on particular sites. The high chemical shift of 105 ppm to 119 ppm was a property of the MWW phase zeolite was not observed yet. The Si0.33 (MOR phase) sample contained at least one faint peak at −99 ppm and two peaks at −106 ppm and −112 ppm, respectively. These peaks were attributed to three distinct types of Si(nAl), where nAl is the number of aluminum atoms connected to silicon via oxygen. Si(0Al) is resonance at −112 ppm, Si(1Al) is resonance at −106 ppm, and Si(2Al) resonance at −99 ppm, respectively. At a higher Si/Al ratio sample involving Si2 and Si3, a change was observed when the peaks were intensified at −111 ppm, aiming for a narrow distribution of crystallography that contrasts with the samples of MCM-22 and Si0.5. These results also confirm the tetrahedral ($T_d$) bonds of Si(0Al) are highly dominant within the structure due to the higher content of silicon atoms.

Figure 11:
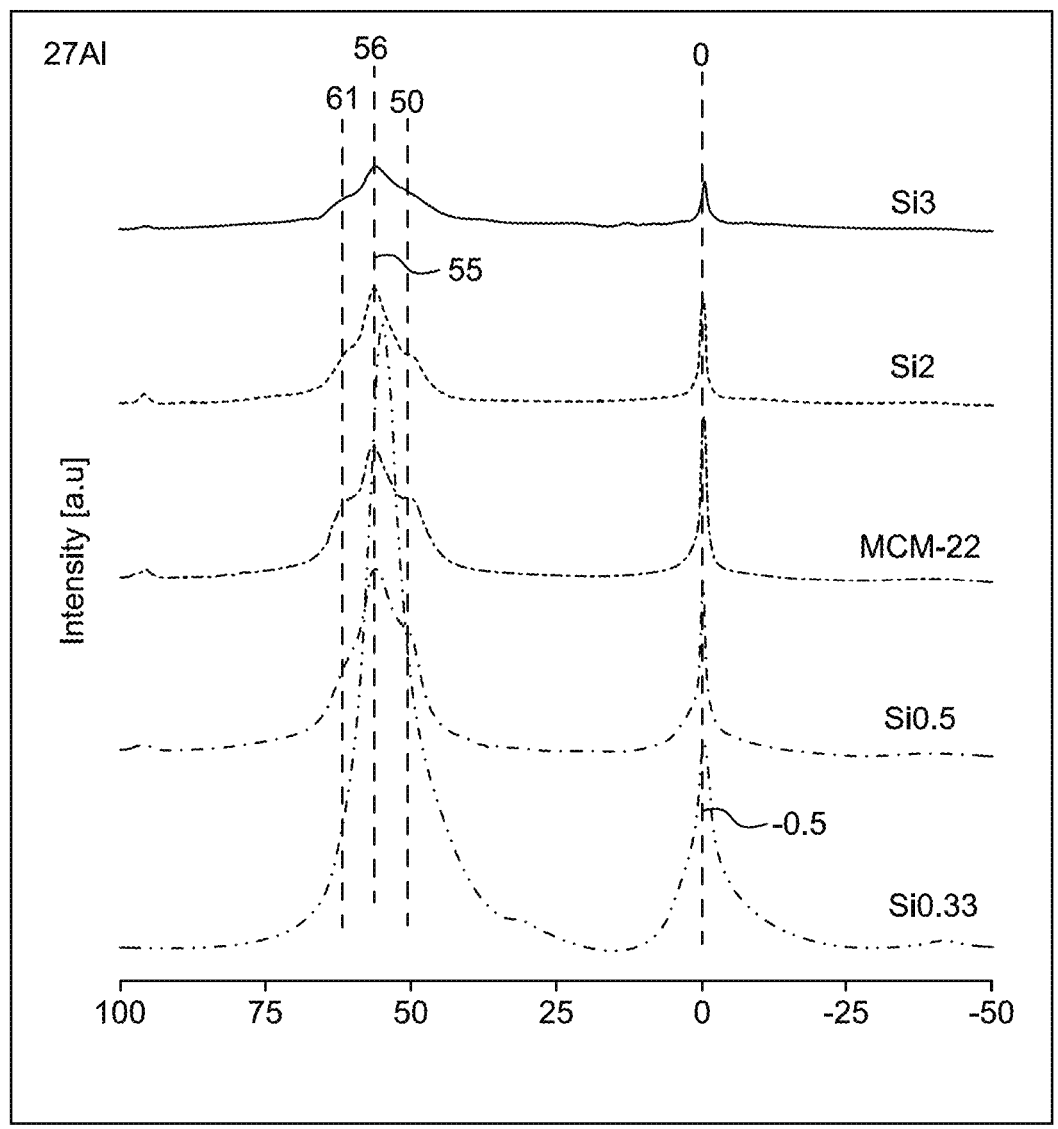
FIG. 11 shows $^{27}Al$ NMR analysis for MCM-22 with different $SiO_2/Al_2O_3$ ratios, according to certain embodiments.

FIG. 11 shows the peaks for 27Al from the base model MCM-22, including at least four shift chemicals: 61, 56, 50, and 0 ppm. These findings demonstrate that the zeolite contained an additional tetrahedral (Td) with 50 and 56 ppm resonances instead of octahedral resonances with extra-framework (EF) sites at 0 ppm. The presence of more than one devoted to resonance in a zeolite structure was unusual. Further, the average angle for each peak at 50 ppm, 56 ppm, and 60 ppm is 164°, 152°, and 142°, respectively. At a lower Si/Al ratio (Si0.33 and Si0.5), the extra framework aluminum intensity was higher than the base model by the ratio over the base model. In contrast, at a higher Si/Al ratio (Si2 and Si3), the extra framework aluminum intensity was reduced from the base model MCM-22. In addition, sample Si0.33 showed two noticeable peaks resonance at 55 ppm, describing aluminum concentration in tetrahedrally coordinated $AlO_4$, and at −0.5 ppm, describing resonance aluminum content in octahedrally coordinated $AlO_6$. These two peaks confirm an MOR phase, as shown by XRD and SEM.

Example 12: Catalytic Performance for Cracking of n-Dodecane

Figure 12:
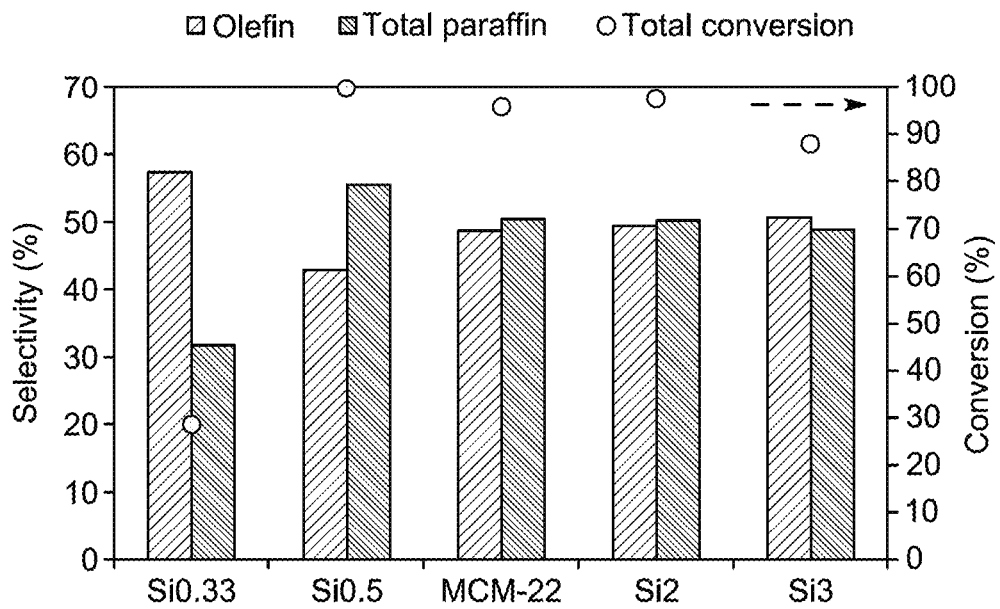
FIG. 12 is a graph depicting conversion and distribution products for cracking of n-dodecane over different $SiO_2/Al_2O_3$ ratios of MCM-22, according to certain embodiments.
Figure 13:
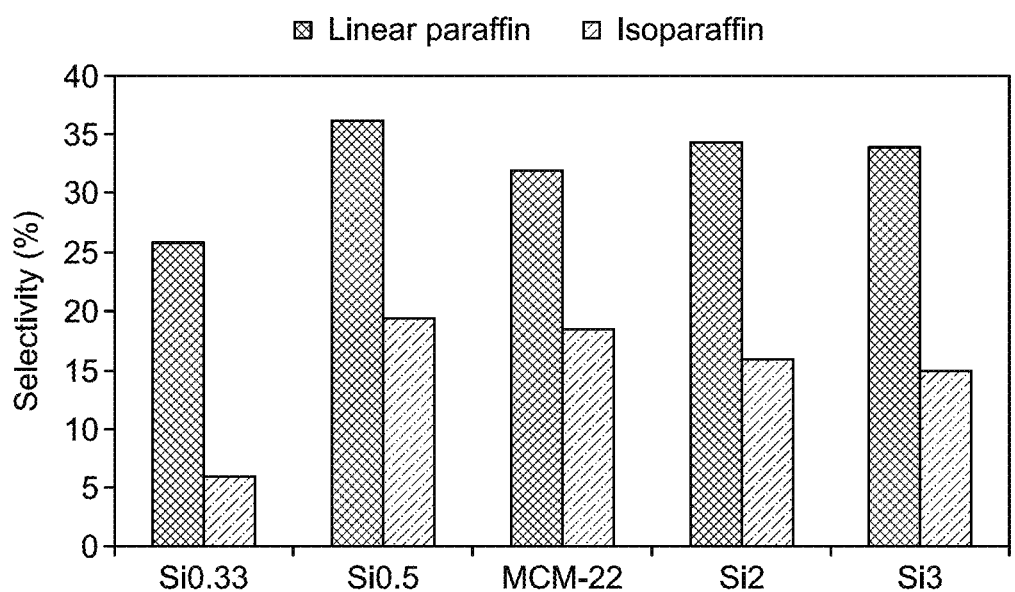
FIG. 13 is a graph depicting the selectivity of linear paraffin and isoparaffin by cracking n-dodecane over different $SiO_2/Al_2O_3$ ratios, according to certain embodiments.

Converting n-dodecane into chemical derivatives like olefins and paraffin compounds was proven to be a stable process using the basic model catalyst MCM-22. Pure n-dodecane was chosen as a model for evaluating the catalytic performance of H-form MCM-22 with various $SiO_2/Al_2O_3$ ratios. The n-dodecane was cracked over a range of $SiO_2/Al_2O_3$ of MCM-22, and the resulting conversion and distribution products are shown in FIG. 12. Further, FIG. 13 illustrates the selectivity of linear paraffin and isoparaffin. As a preliminary investigation, the reaction temperature was set at 350° C. to evaluate the activity of the catalyst and avoid the contribution of homogeneous reaction at the higher cracking temperature, typically established at 550° C. All layered zeolites perform well in converting pure n-dodecane for cracking reactions, with conversion rates of 99.9% for Si0.5, 95.8% for MCM-22, 97.6% Si2, and 88% for Si3, respectively. The conversion rates of 99.9% over the Si0.5 sample were associated with porous structure and external surface area, confirmed by $N_2$ adsorption-desorption analysis in the earlier sections. Meanwhile, the sample Si0.3, which was found to possess the MOR phase, had the lowest conversion value of about 28.7%. The sample Si0.3 has less contact with active sites because there is lesser pore volume, as depicted in Table 4. The acidity and porous structure of the catalyst affected the formation of olefins. Strong acid sites caused catalysts to deactivate rapidly due to coking. Si0.5 exhibited a value for both low-temperature and high-temperature acid density for the MWW phase compared to the other samples confirmed by $NH_3$ adsorption. Porous structure played a role by preventing the formation of large hydrocarbons that are transformed into high-boiling carbonaceous materials. Since catalytic cracking occurs at high temperatures while steam is present, high hydrothermal stability of the catalyst is needed. In addition, unlike other MWW and Kenyaite phases, the MOR phase has a unique framework that was not built using an interlayered structure and super cage void.

The layered structure affected the catalytic cracking of long paraffin hydrocarbons like n-dodecane. The longer hydrocarbon source (C>>10) necessitates a larger porous material to contain a higher degree of the carbon chain in terms of morphology and structural requirements. As a result, the super cage feature within the layered material is advantageous for breaking this specific feed. In an example, sample Si0.5 has a high surface area of 457 $m^2/g$ and a high mesopore volume of up to 0.22 $cm^3/g$, as shown in Table 4, leading to the n-dodecane conversion of almost 100%, as depicted in FIG. 12.

Figure 14:
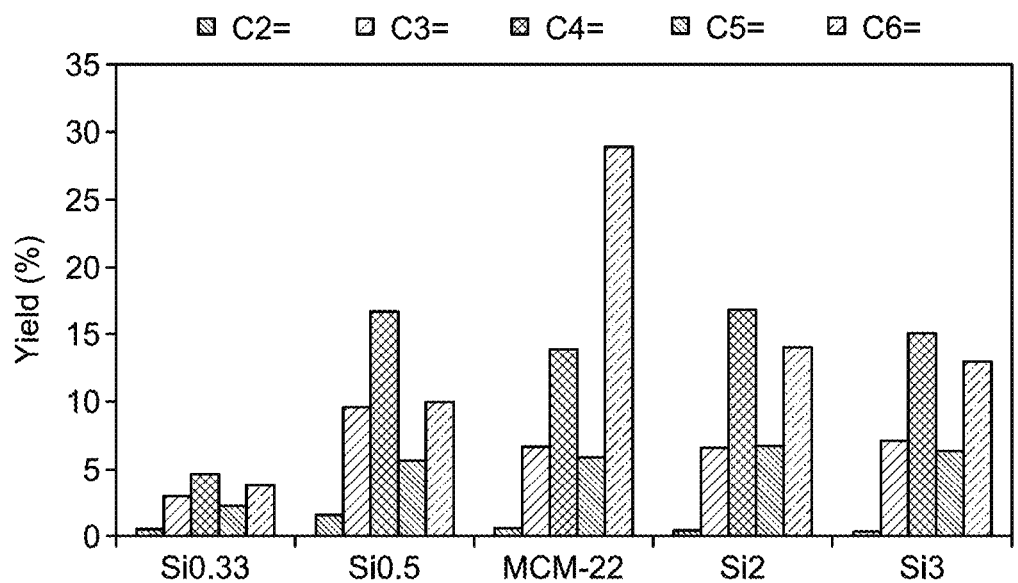
FIG. 14 is a graph depicting the yield of olefin obtained by catalytic cracking of n-dodecane over different $SiO_2/Al_2O_3$ ratios, according to certain embodiments.
Figure 15:
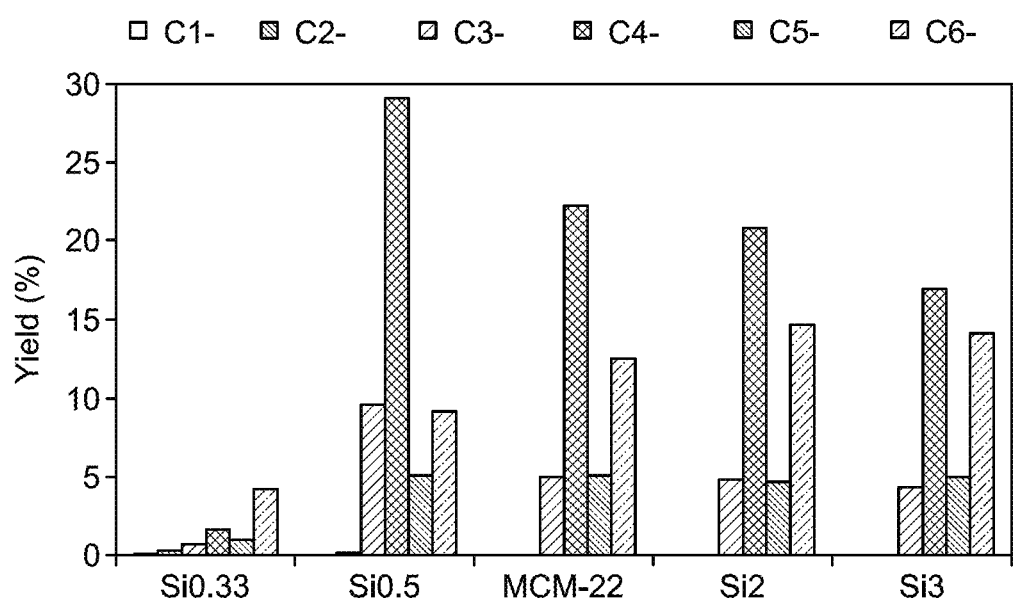
FIG. 15 is a graph depicting the yield of paraffins after the catalytic cracking of n-dodecane over different $SiO_2/Al_2O_3$ ratios, according to certain embodiments.

Furthermore, the sample Si0.33 attained a selectivity ratio of olefinic products over paraffinic products greater than one. Layered material yielded an identical selectivity ratio between olefin and paraffin products. For all ratios of $SiO_2$ and $Al_2O_3$, linear paraffin predominated the final product over isoparaffinic paraffin. In contrast, the tendency is upward for linear paraffin and downward for layered-type zeolite samples like Si0.5, MCM-22, Si2, and Si3. FIG. 14 and FIG. 15 depicts the yield of olefins and paraffinic products, respectively. The distribution of olefinic products was found along the hydrocarbon chain from $C_1$ to $C_6$. Layered materials (sample Si0.5, MCM-22, Si2, and Si3) yield propylene and butylene at around 7% and 14%, respectively. In contrast, the MOR phase in sample Si0.33 produced a low yield of olefinic products compared to the rest of the sample. Moreover, $C_6$ olefin products were abundant in the base model MCM-22, whereas ethylene-produced products were barely detectable in any samples. The paraffinic yield of MWW zeolite varies depending on the $SiO_2/Al_2O_3$ ratio. Propane ($C_3$) and butane ($C_4$) products yield a decreasing trend for layered zeolite material (Si0.5, MCM-22, Si2, and Si3), whereas pentane ($C_5$) products yield a stable value of ca. 4%. Compared to layered zeolitic materials, the sample Si0.33 with the MOR phase yielded a relatively low yield of every paraffinic product. As the materials convert into the MWW and Kenyaite phases, hexane ($C_6$) product production was observed.

Numerous modifications and variations of the present disclosure are possible in light of the above teachings. It is, therefore, to be understood that within the scope of the appended claims, the invention may be practiced otherwise than as specifically described herein.

The invention claimed is:

1. A method of cracking a hydrocarbon, comprising:
contacting the hydrocarbon with an aluminosilicate zeolite catalyst to produce a cracking product,
wherein the aluminosilicate zeolite comprises an MCM-22 crystal phase and a weight ratio of $SiO_2$ to $Al_2O_3$ of 19-28.8:1,
wherein particles of the aluminosilicate zeolite have a flake shape with an average longest dimension of 10-50 nm,
wherein the flakes are stacked on top of one another, and
wherein the aluminosilicate zeolite has an average pore size of 2-5 nm.

2. The method of claim 1, wherein the aluminosilicate zeolite has a relative crystallinity of 50-100%.

3. The method of claim 1, wherein the aluminosilicate zeolite has an average crystal size of 10-30 nm.

4. The method of claim 1, wherein the aluminosilicate zeolite has a BET surface area of 400-500 $m^2/g$.

5. The method of claim 1, wherein the aluminosilicate zeolite has an external surface area of 100-150 $m^2/g$.

6. The method of claim 1, wherein the aluminosilicate zeolite has an average crystal size of about 15 nm.

7. The method of claim 1, wherein the aluminosilicate zeolite has a mesopore volume of 0.1-0.3 $cm^3/g$ and a micropore volume of 0.01-0.2 $cm^3/g$.

8. The method of claim 1, wherein the aluminosilicate zeolite comprises 0.1-5 wt. % Al, 40-50 wt. % Si, and 50-60 wt. % O, based on a total weight of the aluminosilicate zeolite.

9. The method of claim 1, wherein the aluminosilicate zeolite has an acid density of 0.2-0.6 mmol/g.

10. The method of claim 1, wherein the contacting is at a temperature of 200-600° C.

11. The method of claim 1, wherein the hydrocarbon has 5-20 carbon atoms.

12. The method of claim 1, wherein the hydrocarbon is n-dodecane.

13. The method of claim 1, wherein the catalyst has a conversion rate of at least 90% to the cracking product.

14. The method of claim 1, wherein the cracking product includes at least one selected from the group consisting of olefins and paraffins.

15. The method of claim 1, wherein the cracking product includes both olefins and paraffins, and
a ratio of paraffins to olefins is 1:1 to 2:1.

16. The method of claim 1, wherein the cracking product includes at least 30% linear paraffins.

17. The method of claim 1, wherein the cracking product includes at least one compound having 1-6 carbon atoms.

18. The method of claim 1, wherein the aluminosilicate zeolite has a weight ratio of $SiO_2$ to $Al_2O_3$ of 28.8:1, wherein the catalyst has a conversion rate of 99.9% to the cracking product,
wherein the hydrocarbon is n-dodecane,
wherein the cracking product includes at least 25% of paraffin compounds having 4 carbon atoms, and
wherein the cracking product includes at least 15% of olefin compounds having 4 carbon atoms.

19. The method of claim 1, wherein the catalyst has a conversation rate of pure n-dodecane at 350° C. of 99.9% or more.

* * * * *